(12) United States Patent
Allis et al.

(10) Patent No.: US 9,388,213 B2
(45) Date of Patent: Jul. 12, 2016

(54) POLYCOMB REPRESSIVE COMPLEX 2 (PRC2) INHIBITORS AND USES THEREOF

(71) Applicant: The Rockefeller University, New York, NY (US)

(72) Inventors: C. David Allis, Princeton, NJ (US); Peter Lewis, Madison, WI (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 14/023,223

(22) Filed: Sep. 10, 2013

(65) Prior Publication Data

US 2014/0107039 A1  Apr. 17, 2014

Related U.S. Application Data

(60) Provisional application No. 61/698,779, filed on Sep. 10, 2012.

(51) Int. Cl.
  *C07K 7/06* (2006.01)
  *C07K 7/08* (2006.01)
  *A61K 47/48* (2006.01)

(52) U.S. Cl.
  CPC .............. *C07K 7/06* (2013.01); *A61K 47/48246* (2013.01); *C07K 7/08* (2013.01)

(58) Field of Classification Search
  CPC ....... A61K 47/48246; C07K 7/06; C07K 7/08
  USPC ................. 514/19.3, 21.6; 530/326, 327, 350
  See application file for complete search history.

(56) References Cited

U.S. PATENT DOCUMENTS

2007/0044171 A1 * 2/2007 Kovalic et al. ................ 800/278

FOREIGN PATENT DOCUMENTS

CA  WO2013075237 A1 * 5/2013 ............. C07K 14/47

OTHER PUBLICATIONS

Shakhashiri, www.scifun.org, Chemical of the Week, Water, Jan. 2011.*
UniProt Database, Histone H3, Protein Accession B4YSR1, sequence on p. 2, Sep. 2008.*
Sequence Identification Listing for Seq ID No. 152402 for US20070044171 A1. 2007.*
Sequence Identification Listing for WO2013075237 (2012), Seq ID Nos. 1-9, accessed from WIPO website.*
Medical definition of Moiety, http://medical-dictionary.thefreedictionary.com/p/moiety, accessed on Jun. 26, 2014.*
Kimberly H Kim, Targeting EZH2 in cancer, vol. 22 | No. 2 | Feb. 2016 nature medicine.*
Koki Ueda, Inhibition of histone methyltransferase EZH2 depletes leukemia stem cell of mixed lineage leukemia fusion leukemia through upregulation of p. 16, Cancer Sci | May 2014 | vol. 105 | No. 5 | 512-519.*
Chunhua Xu, EZH2 regulates cancer cell migration through repressing TIMP-3 in non-small cell lung cancer, Med Oncol (2013) 30:713.*
Roberta Ciarapica, Enhancer of zeste homolog 2 (EZH2) in pediatric soft tissue sarcomas: first implications, BMC Medicine 2011, 9:63.*
Jeffrey A. Simon, Roles of the EZH2 histone methyltransferase in cancer epigenetics, Mutation Research 647 (2008) 21-29.*
Chase et al., "Aberrations of EZH2 in Cancer," Clin. Cancer Res. 17:2613-2618 (2011).
Jiao et al., "DAXX/ATRX, MEN1 and mTOR Pathway Genes are Frequently Altered in Pancreatic Neuroendocrine Tumors," Science 331(6021):1199-1203 (2011).
Schwartzentruber et al., "Driver Mutations in Histone H3.3 and Chromatin Remodelling Genes in Paediatric Glioblastoma," Nature 482(7384):226-31 (2012).
Dawson & Kouzarides, "Cancer Epigenetics: From Mechanism to Therapy," Cell 150:12-27 (2012).
Lewis et al., "Inhibition of PRC2 Activity by a Gain-of-Function H3 Mutation Found in Pediatric Glioblastoma," Science 340(6134):857-861 (2013).
Lewis, "Inhibition of PRC2 Methyltransferase Activity by Gain-of-Function H3 Mutations Found in Pediatric Glioblastoma," Presentation given at Temasek Life Science Laboratory, Singapore (Sep. 17, 2012).
Lewis, "Inhibition of PRC2 Methyltransferase Activity by Gain-of-Function H3 Mutations Found in Pediatric Glioblastoma," Presentation given at Cold Spring Harbor Meeting (Sep. 10, 2012).

* cited by examiner

*Primary Examiner* — James H Alstrum Acevedo
*Assistant Examiner* — Erinne Dabkowski
(74) *Attorney, Agent, or Firm* — LeClairRyan, a Professional Corporation

(57) ABSTRACT

The present invention relates to Polycomb Repressive Complex 2 (PRC2) peptide inhibitors and their use for the treatment of cancer and other conditions associated with aberrant PRC2 methyltransferase activity.

17 Claims, 7 Drawing Sheets

SEQUENCE LISTING

<160> NUMBER OF SEQ ID NOS: 57

<210> SEQ ID NO 1
<211> LENGTH: 5
<212> TYPE: PRT
<213> ORGANISM: Artificial
<220> FEATURE:
<223> OTHER INFORMATION: Histone H3

<400> SEQUENCE: 1

Ala Ala Arg Met Ser
1               5

<210> SEQ ID NO 2
<211> LENGTH: 135
<212> TYPE: PRT
<213> ORGANISM: Artificial
<220> FEATURE:
<223> OTHER INFORMATION: Histone H3.1

<400> SEQUENCE: 2

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ala Thr
                20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Cys
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 3
<211> LENGTH: 135
<212> TYPE: PRT
<213> ORGANISM: Artificial
<220> FEATURE:
<223> OTHER INFORMATION: Histone H3.3

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ser Thr
                20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

```
Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
        130             135

<210> SEQ ID NO 4
<211> LENGTH: 11
<212> TYPE: PRT
<213> ORGANISM: Artificial
<220> FEATURE:
<223> OTHER INFORMATION: Histone H3
<220> FEATURE:
<221> NAME/KEY: MISC_FEATURE
<222> LOCATION: (1)..(1)
<223> OTHER INFORMATION: Xaa at position 1 is any amino acid reisdue
<220> FEATURE:
<221> NAME/KEY: MISC_FEATURE
<222> LOCATION: (7)..(7)
<223> OTHER INFORMATION: Xaa at position 7 is any amino acid reisdue
<220> FEATURE:
<221> NAME/KEY: MISC_FEATURE
<222> LOCATION: (9)..(10)
<223> OTHER INFORMATION: Xaa at positions 9 and 10 is any amino acid
      reisdue

<400> SEQUENCE: 4

Xaa Ala Ala Arg Met Ser Xaa Pro Xaa Xaa Gly
1               5                   10

<210> SEQ ID NO 5
<211> LENGTH: 11
<212> TYPE: PRT
<213> ORGANISM: Artificial
<220> FEATURE:
<223> OTHER INFORMATION: Histone H3

<400> SEQUENCE: 5

Lys Ala Ala Arg Met Ser Ala Pro Ser Thr Gly
1               5                   10

<210> SEQ ID NO 6
<211> LENGTH: 11
<212> TYPE: PRT
<213> ORGANISM: Artificial
<220> FEATURE:
<223> OTHER INFORMATION: Histone H3

<400> SEQUENCE: 6

Lys Ala Ala Arg Met Ser Ala Pro Thr Thr Gly
1               5                   10

<210> SEQ ID NO 7
<211> LENGTH: 11
<212> TYPE: PRT
<213> ORGANISM: Artificial
<220> FEATURE:
<223> OTHER INFORMATION: Histone H3

<400> SEQUENCE: 7

Lys Ala Ala Arg Met Ser Ala Pro Ala Thr Gly
1               5                   10

<210> SEQ ID NO 8
<211> LENGTH: 11
<212> TYPE: PRT
```

<213> ORGANISM: Artificial
<220> FEATURE:
<223> OTHER INFORMATION: Histone H3

<400> SEQUENCE: 8

Arg Ala Ala Arg Met Ser Ala Pro Ser Thr Gly
1               5                   10

<210> SEQ ID NO 9
<211> LENGTH: 11
<212> TYPE: PRT
<213> ORGANISM: Artificial
<220> FEATURE:
<223> OTHER INFORMATION: Histone H3

<400> SEQUENCE: 9

Arg Ala Ala Arg Met Ser Ala Pro Thr Thr Gly
1               5                   10

<210> SEQ ID NO 10
<211> LENGTH: 11
<212> TYPE: PRT
<213> ORGANISM: Artificial
<220> FEATURE:
<223> OTHER INFORMATION: Histone H3

<400> SEQUENCE: 10

Arg Ala Ala Arg Met Ser Ala Pro Ala Thr Gly
1               5                   10

<210> SEQ ID NO 11
<211> LENGTH: 11
<212> TYPE: PRT
<213> ORGANISM: Artificial
<220> FEATURE:
<223> OTHER INFORMATION: Histone H3

<400> SEQUENCE: 11

Lys Ala Ala Arg Met Ser Ser Pro Ser Thr Gly
1               5                   10

<210> SEQ ID NO 12
<211> LENGTH: 11
<212> TYPE: PRT
<213> ORGANISM: Artificial
<220> FEATURE:
<223> OTHER INFORMATION: Histone H3

<400> SEQUENCE: 12

Lys Ala Ala Arg Met Ser Ser Pro Thr Thr Gly
1               5                   10

<210> SEQ ID NO 13
<211> LENGTH: 11
<212> TYPE: PRT
<213> ORGANISM: Artificial
<220> FEATURE:
<223> OTHER INFORMATION: Histone H3

<400> SEQUENCE: 13

Lys Ala Ala Arg Met Ser Ser Pro Ala Thr Gly
1               5                   10

<210> SEQ ID NO 14
<211> LENGTH: 11
<212> TYPE: PRT
<213> ORGANISM: Artificial

```
<220> FEATURE:
<223> OTHER INFORMATION: Histone H3

<400> SEQUENCE: 14

Arg Ala Ala Arg Met Ser Ser Pro Ser Thr Gly
1               5                   10

<210> SEQ ID NO 15
<211> LENGTH: 11
<212> TYPE: PRT
<213> ORGANISM: Artificial
<220> FEATURE:
<223> OTHER INFORMATION: Histone H3

<400> SEQUENCE: 15

Arg Ala Ala Arg Met Ser Ser Pro Thr Thr Gly
1               5                   10

<210> SEQ ID NO 16
<211> LENGTH: 11
<212> TYPE: PRT
<213> ORGANISM: Artificial
<220> FEATURE:
<223> OTHER INFORMATION: Histone H3

<400> SEQUENCE: 16

Arg Ala Ala Arg Met Ser Ser Pro Ala Thr Gly
1               5                   10

<210> SEQ ID NO 17
<211> LENGTH: 11
<212> TYPE: PRT
<213> ORGANISM: Artificial
<220> FEATURE:
<223> OTHER INFORMATION: Histone H3

<400> SEQUENCE: 17

Lys Ala Ala Arg Met Ser Ala Pro Ser Ser Gly
1               5                   10

<210> SEQ ID NO 18
<211> LENGTH: 11
<212> TYPE: PRT
<213> ORGANISM: Artificial
<220> FEATURE:
<223> OTHER INFORMATION: Histone H3

<400> SEQUENCE: 18

Lys Ala Ala Arg Met Ser Ala Pro Thr Ser Gly
1               5                   10

<210> SEQ ID NO 19
<211> LENGTH: 11
<212> TYPE: PRT
<213> ORGANISM: Artificial
<220> FEATURE:
<223> OTHER INFORMATION: Histone H3

<400> SEQUENCE: 19

Lys Ala Ala Arg Met Ser Ala Pro Ala Ser Gly
1               5                   10

<210> SEQ ID NO 20
<211> LENGTH: 11
<212> TYPE: PRT
<213> ORGANISM: Artificial
<220> FEATURE:
```

<223> OTHER INFORMATION: Histone H3

<400> SEQUENCE: 20

Arg Ala Ala Arg Met Ser Ala Pro Ser Ser Gly
1               5                   10

<210> SEQ ID NO 21
<211> LENGTH: 11
<212> TYPE: PRT
<213> ORGANISM: Artificial
<220> FEATURE:
<223> OTHER INFORMATION: Histone H3

<400> SEQUENCE: 21

Arg Ala Ala Arg Met Ser Ala Pro Thr Ser Gly
1               5                   10

<210> SEQ ID NO 22
<211> LENGTH: 11
<212> TYPE: PRT
<213> ORGANISM: Artificial
<220> FEATURE:
<223> OTHER INFORMATION: Histone H3

<400> SEQUENCE: 22

Arg Ala Ala Arg Met Ser Ala Pro Ala Ser Gly
1               5                   10

<210> SEQ ID NO 23
<211> LENGTH: 11
<212> TYPE: PRT
<213> ORGANISM: Artificial
<220> FEATURE:
<223> OTHER INFORMATION: Histone H3

<400> SEQUENCE: 23

Lys Ala Ala Arg Met Ser Ser Pro Ser Ser Gly
1               5                   10

<210> SEQ ID NO 24
<211> LENGTH: 11
<212> TYPE: PRT
<213> ORGANISM: Artificial
<220> FEATURE:
<223> OTHER INFORMATION: Histone H3

<400> SEQUENCE: 24

Lys Ala Ala Arg Met Ser Ser Pro Thr Ser Gly
1               5                   10

<210> SEQ ID NO 25
<211> LENGTH: 11
<212> TYPE: PRT
<213> ORGANISM: Artificial
<220> FEATURE:
<223> OTHER INFORMATION: Histone H3

<400> SEQUENCE: 25

Lys Ala Ala Arg Met Ser Ser Pro Ala Ser Gly
1               5                   10

<210> SEQ ID NO 26
<211> LENGTH: 11
<212> TYPE: PRT
<213> ORGANISM: Artificial
<220> FEATURE:
<223> OTHER INFORMATION: Histone H3

<400> SEQUENCE: 26

Arg Ala Ala Arg Met Ser Ser Pro Ser Ser Gly
1               5                   10

<210> SEQ ID NO 27
<211> LENGTH: 11
<212> TYPE: PRT
<213> ORGANISM: Artificial
<220> FEATURE:
<223> OTHER INFORMATION: Histone H3

<400> SEQUENCE: 27

Arg Ala Ala Arg Met Ser Ser Pro Thr Ser Gly
1               5                   10

<210> SEQ ID NO 28
<211> LENGTH: 11
<212> TYPE: PRT
<213> ORGANISM: Artificial
<220> FEATURE:
<223> OTHER INFORMATION: Histone H3

<400> SEQUENCE: 28

Arg Ala Ala Arg Met Ser Ser Pro Ala Ser Gly
1               5                   10

<210> SEQ ID NO 29
<211> LENGTH: 11
<212> TYPE: PRT
<213> ORGANISM: Artificial
<220> FEATURE:
<223> OTHER INFORMATION: Histone H3

<400> SEQUENCE: 29

Lys Ala Ala Arg Met Ser Ala Pro Ser Ala Gly
1               5                   10

<210> SEQ ID NO 30
<211> LENGTH: 11
<212> TYPE: PRT
<213> ORGANISM: Artificial
<220> FEATURE:
<223> OTHER INFORMATION: Histone H3

<400> SEQUENCE: 30

Lys Ala Ala Arg Met Ser Ala Pro Thr Ala Gly
1               5                   10

<210> SEQ ID NO 31
<211> LENGTH: 11
<212> TYPE: PRT
<213> ORGANISM: Artificial
<220> FEATURE:
<223> OTHER INFORMATION: Histone H3

<400> SEQUENCE: 31

Lys Ala Ala Arg Met Ser Ala Pro Ala Ala Gly
1               5                   10

<210> SEQ ID NO 32
<211> LENGTH: 11
<212> TYPE: PRT
<213> ORGANISM: Artificial
<220> FEATURE:
<223> OTHER INFORMATION: Histone H3

```
<400> SEQUENCE: 32

Arg Ala Ala Arg Met Ser Ala Pro Ser Ala Gly
1               5                   10

<210> SEQ ID NO 33
<211> LENGTH: 11
<212> TYPE: PRT
<213> ORGANISM: Artificial
<220> FEATURE:
<223> OTHER INFORMATION: Histone H3

<400> SEQUENCE: 33

Arg Ala Ala Arg Met Ser Ala Pro Thr Ala Gly
1               5                   10

<210> SEQ ID NO 34
<211> LENGTH: 11
<212> TYPE: PRT
<213> ORGANISM: Artificial
<220> FEATURE:
<223> OTHER INFORMATION: Histone H3

<400> SEQUENCE: 34

Arg Ala Ala Arg Met Ser Ala Pro Ala Ala Gly
1               5                   10

<210> SEQ ID NO 35
<211> LENGTH: 11
<212> TYPE: PRT
<213> ORGANISM: Artificial
<220> FEATURE:
<223> OTHER INFORMATION: Histone H3

<400> SEQUENCE: 35

Lys Ala Ala Arg Met Ser Ser Pro Ser Ala Gly
1               5                   10

<210> SEQ ID NO 36
<211> LENGTH: 11
<212> TYPE: PRT
<213> ORGANISM: Artificial
<220> FEATURE:
<223> OTHER INFORMATION: Histone H3

<400> SEQUENCE: 36

Lys Ala Ala Arg Met Ser Ser Pro Thr Ala Gly
1               5                   10

<210> SEQ ID NO 37
<211> LENGTH: 11
<212> TYPE: PRT
<213> ORGANISM: Artificial
<220> FEATURE:
<223> OTHER INFORMATION: Histone H3

<400> SEQUENCE: 37

Lys Ala Ala Arg Met Ser Ser Pro Ala Ala Gly
1               5                   10

<210> SEQ ID NO 38
<211> LENGTH: 11
<212> TYPE: PRT
<213> ORGANISM: Artificial
<220> FEATURE:
<223> OTHER INFORMATION: Histone H3

<400> SEQUENCE: 38
```

```
Arg Ala Ala Arg Met Ser Ser Pro Ser Ala Gly
1               5                   10

<210> SEQ ID NO 39
<211> LENGTH: 11
<212> TYPE: PRT
<213> ORGANISM: Artificial
<220> FEATURE:
<223> OTHER INFORMATION: Histone H3

<400> SEQUENCE: 39

Arg Ala Ala Arg Met Ser Ser Pro Thr Ala Gly
1               5                   10

<210> SEQ ID NO 40
<211> LENGTH: 11
<212> TYPE: PRT
<213> ORGANISM: Artificial
<220> FEATURE:
<223> OTHER INFORMATION: Histone H3

<400> SEQUENCE: 40

Arg Ala Ala Arg Met Ser Ser Pro Ala Ala Gly
1               5                   10

<210> SEQ ID NO 41
<211> LENGTH: 15
<212> TYPE: PRT
<213> ORGANISM: Artificial
<220> FEATURE:
<223> OTHER INFORMATION: Histone H3
<220> FEATURE:
<221> NAME/KEY: MISC_FEATURE
<222> LOCATION: (2)..(2)
<223> OTHER INFORMATION: Xaa at position 2 comprises any amino acid
      residue
<220> FEATURE:
<221> NAME/KEY: MISC_FEATURE
<222> LOCATION: (8)..(8)
<223> OTHER INFORMATION: Xaa at position 8 comprises any amino acid
      residue
<220> FEATURE:
<221> NAME/KEY: MISC_FEATURE
<222> LOCATION: (10)..(11)
<223> OTHER INFORMATION: Xaa at positions 10 and 11 comprises any amino
      acid residue

<400> SEQUENCE: 41

Thr Xaa Ala Ala Arg Met Ser Xaa Pro Xaa Xaa Gly Gly Val Lys
1               5                   10                  15

<210> SEQ ID NO 42
<211> LENGTH: 15
<212> TYPE: PRT
<213> ORGANISM: Artificial
<220> FEATURE:
<223> OTHER INFORMATION: Histone H3

<400> SEQUENCE: 42

Thr Lys Ala Ala Arg Met Ser Ala Pro Ala Thr Gly Gly Val Lys
1               5                   10                  15

<210> SEQ ID NO 43
<211> LENGTH: 15
<212> TYPE: PRT
<213> ORGANISM: Artificial
<220> FEATURE:
<223> OTHER INFORMATION: Histone H3
```

<400> SEQUENCE: 43

Thr Lys Ala Ala Arg Met Ser Ala Pro Ala Thr Gly Gly Val Lys
1               5                   10                  15

<210> SEQ ID NO 44
<211> LENGTH: 20
<212> TYPE: PRT
<213> ORGANISM: Artificial
<220> FEATURE:
<223> OTHER INFORMATION: Histone H3
<220> FEATURE:
<221> NAME/KEY: MISC_FEATURE
<222> LOCATION: (6)..(6)
<223> OTHER INFORMATION: Xaa at position 6 comprises any amino acid
      reisdue
<220> FEATURE:
<221> NAME/KEY: MISC_FEATURE
<222> LOCATION: (12)..(12)
<223> OTHER INFORMATION: Xaa at position 12 comprises any amino acid
      reisdue
<220> FEATURE:
<221> NAME/KEY: MISC_FEATURE
<222> LOCATION: (14)..(15)
<223> OTHER INFORMATION: Xaa at positions 14 and 15 comprises any amino
      acid reisdue

<400> SEQUENCE: 44

Lys Gln Leu Ala Thr Xaa Ala Ala Arg Met Ser Xaa Pro Xaa Xaa Gly
1               5                   10                  15

Gly Val Lys Lys
            20

<210> SEQ ID NO 45
<211> LENGTH: 20
<212> TYPE: PRT
<213> ORGANISM: Artificial
<220> FEATURE:
<223> OTHER INFORMATION: Histone H3

<400> SEQUENCE: 45

Lys Gln Leu Ala Thr Lys Ala Ala Arg Met Ser Ala Pro Ala Thr Gly
1               5                   10                  15

Gly Val Lys Lys
            20

<210> SEQ ID NO 46
<211> LENGTH: 20
<212> TYPE: PRT
<213> ORGANISM: Artificial
<220> FEATURE:
<223> OTHER INFORMATION: Histone H3

<400> SEQUENCE: 46

Lys Gln Leu Ala Thr Lys Ala Ala Arg Met Ser Ala Pro Ser Thr Gly
1               5                   10                  15

Gly Val Lys Lys
            20

<210> SEQ ID NO 47
<211> LENGTH: 12
<212> TYPE: PRT
<213> ORGANISM: Artificial
<220> FEATURE:
<223> OTHER INFORMATION: Trans-Activator of Transcription
<220> FEATURE:
<221> NAME/KEY: MISC_FEATURE
<222> LOCATION: (1)..(1)
<223> OTHER INFORMATION: Xaa at position 1 is NH2

```
<220> FEATURE:
<221> NAME/KEY: MISC_FEATURE
<222> LOCATION: (12)..(12)
<223> OTHER INFORMATION: Xaa at position 12 is COOH

<400> SEQUENCE: 47

Xaa Gly Arg Lys Lys Arg Arg Gln Arg Arg Xaa
1               5                   10

<210> SEQ ID NO 48
<211> LENGTH: 13
<212> TYPE: PRT
<213> ORGANISM: Artificial
<220> FEATURE:
<223> OTHER INFORMATION: Trans-Activator of Transcription
<220> FEATURE:
<221> NAME/KEY: MISC_FEATURE
<222> LOCATION: (1)..(1)
<223> OTHER INFORMATION: Xaa at position 1 is NH2
<220> FEATURE:
<221> NAME/KEY: MISC_FEATURE
<222> LOCATION: (2)..(2)
<223> OTHER INFORMATION: Xaa at position 2 is any amino acid residue
<220> FEATURE:
<221> NAME/KEY: MISC_FEATURE
<222> LOCATION: (12)..(12)
<223> OTHER INFORMATION: Xaa at position 12 is any amino acid residue
<220> FEATURE:
<221> NAME/KEY: MISC_FEATURE
<222> LOCATION: (13)..(13)
<223> OTHER INFORMATION: Xaa at position 13 is COOH

<400> SEQUENCE: 48

Xaa Xaa Arg Lys Lys Arg Arg Gln Arg Arg Xaa Xaa
1               5                   10

<210> SEQ ID NO 49
<211> LENGTH: 13
<212> TYPE: PRT
<213> ORGANISM: Artificial
<220> FEATURE:
<223> OTHER INFORMATION: Trans-Activator of Transcription
<220> FEATURE:
<221> NAME/KEY: MISC_FEATURE
<222> LOCATION: (1)..(1)
<223> OTHER INFORMATION: Xaa at position 1 is NH2
<220> FEATURE:
<221> NAME/KEY: MISC_FEATURE
<222> LOCATION: (2)..(2)
<223> OTHER INFORMATION: Xaa at position 2 is any amino acid residue
<220> FEATURE:
<221> NAME/KEY: MISC_FEATURE
<222> LOCATION: (12)..(12)
<223> OTHER INFORMATION: Xaa at position 12 is any amino acid residue
<220> FEATURE:
<221> NAME/KEY: MISC_FEATURE
<222> LOCATION: (13)..(13)
<223> OTHER INFORMATION: Xaa at position 13 is COOH

<400> SEQUENCE: 49

Xaa Xaa Arg Arg Arg Gln Arg Arg Lys Lys Arg Xaa Xaa
1               5                   10

<210> SEQ ID NO 50
<211> LENGTH: 4
<212> TYPE: PRT
<213> ORGANISM: Artificial
<220> FEATURE:
<223> OTHER INFORMATION: Linker sequence

<400> SEQUENCE: 50

Gly Ser Gly Ser
```

<210> SEQ ID NO 51
<211> LENGTH: 5
<212> TYPE: PRT
<213> ORGANISM: Artificial
<220> FEATURE:
<223> OTHER INFORMATION: Linker sequence

<400> SEQUENCE: 51

Gly Ser Gly Ser Gly
1               5

<210> SEQ ID NO 52
<211> LENGTH: 8
<212> TYPE: PRT
<213> ORGANISM: Artificial
<220> FEATURE:
<223> OTHER INFORMATION: Nuclear transport peptide

<400> SEQUENCE: 52

Pro Pro Lys Lys Lys Arg Lys Val
1               5

<210> SEQ ID NO 53
<211> LENGTH: 469
<212> TYPE: DNA
<213> ORGANISM: Artificial
<220> FEATURE:
<223> OTHER INFORMATION: Histone H3.1

<400> SEQUENCE: 53
atggctcgca ctaagcaaac tgctcggaag tctactggtg gcaaggcgcc acgcaaacag      60
ttggccacta aggcagcccg caaaagcgct ccggccaccg gcggcgtgaa aaagccccac     120
cgctaccggc cgggcaccgt ggctctgcgc gagatccgcc gttatcagaa gtccactgaa     180
ctgcttattc gtaaactacc tttccagcgc ctggtgcgcg agattgcgca ggactttaaa     240
acagacctgc gtttccagag ctccgctgtg atggctctgc aggaggcgtg cgaggcctac     300
ttggtagggc tatttgagga cactaacctg tgcgccatcc acgccaagcg cgtcactatc     360
atgcccaagg acatccagct cgcccgccgc atccgcggag agagggcgtg attactgtgg     420
tctctctgac ggtccaagca aaggctcttt tcagagccac cacctttttc                469

<210> SEQ ID NO 54
<211> LENGTH: 1077
<212> TYPE: DNA
<213> ORGANISM: Artificial
<220> FEATURE:
<223> OTHER INFORMATION: Histone H3.3

<400> SEQUENCE: 54
gtcagccatc tttcaattgt gttcgcagcc gccgccgcgc cgccgtcgct ctccaacgcc      60
agcgccgcct ctcgctcgcc gagctccagc cgaaggagaa ggggggtaag taaggaggtc     120
tctgtaccat ggctcgtaca aagcagactg cccgcaaatc gaccggtggt aaagcaccca     180
ggaagcaact ggctacaaaa gccgctcgca gagtgcgcc ctctactgga ggggtgaaga     240
aacctcatcg ttacaggcct ggtactgtgg cgctccgtga aattagacgt tatcagaagt     300
ccactgaact tctgattcgc aaacttcctt tccagcgtct ggtgcgagaa attgctcagg     360
actttaaaac agatctgcgc ttccagagcg cagctatcgg tgctttgcag gaggcaagtg     420
aggcctatct ggttggcctt tttgaagaca ccaacctgtg tgctatccat gccaaacgtg     480

```
taacaattat gccaaaagac atccagctag cacgccgcat acgtggagaa cgtgcttaag    540
aatccactat gatgggaaac atttcattct caaaaaaaaa aaaaaaaatt tctcttcttc    600
ctgttattgg tagttctgaa cgttagatat tttttttcca tggggtcaaa aggtacctaa    660
gtatatgatt gcgagtggaa aataggggga cagaaatcag gtattggcag tttttccatt    720
ttcatttgtg tgtgaatttt taatataaat gcggagacgt aaagcattaa tgcaagttaa    780
aatgtttcag tgaacaagtt tcagcggttc aactttataa taattataaa taaacctgtt    840
aaattttcct ggacaatgcc agcatttgga ttttttaaa acaagtaaat ttcttattga     900
tggcaactaa atggtgtttg tagcattttt atcatacagt agattccatc cattcactat    960
acttttctaa ctgagttgtc ctacatgcaa gtacatgttt ttaatgttgt ctgtcttctg   1020
tgctgttcct gtaagtttgc tattaaaata cattaaacta taaaaaaaaa aaaaaaa     1077
```

<210> SEQ ID NO 55
<211> LENGTH: 9
<212> TYPE: PRT
<213> ORGANISM: Artificial
<220> FEATURE:
<223> OTHER INFORMATION: Histone H3

<400> SEQUENCE: 55

Ala Ala Arg Met Ser Ala Pro Ser Cys
1               5

<210> SEQ ID NO 56
<211> LENGTH: 9
<212> TYPE: PRT
<213> ORGANISM: Artificial
<220> FEATURE:
<223> OTHER INFORMATION: Histone H3

<400> SEQUENCE: 56

Ala Ala Arg Met Ser Ala Pro Ala Cys
1               5

<210> SEQ ID NO 57
<211> LENGTH: 162
<212> TYPE: PRT
<213> ORGANISM: Artificial
<220> FEATURE:
<223> OTHER INFORMATION: Histone H3.3

<400> SEQUENCE: 57

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala

-continued

```
            115                 120                 125
Arg Arg Ile Arg Gly Glu Arg Ala Ala Ala Gly Gly Asp Tyr Lys
        130                 135                 140

Asp Asp Asp Asp Lys Ser Ala Ala Gly Gly Tyr Pro Tyr Asp Val Pro
145                 150                 155                 160

Asp Ala
```

US 9,388,213 B2

POLYCOMB REPRESSIVE COMPLEX 2 (PRC2) INHIBITORS AND USES THEREOF

This application claims the priority benefit of U.S. Provisional Patent Application Ser. No. 61/698,779, filed Sep. 10, 2012, which is hereby incorporated by reference in its entirety.

This invention was made with government support under grant number GM-040922-27 awarded by the National Institutes of Health. The government has certain rights in this invention.

FIELD OF THE INVENTION

The present invention relates to PRC2 inhibitors and their use for the treatment of cancer and other conditions associated with PRC2 activity.

BACKGROUND OF THE INVENTION

Post-translational modifications of the amino-terminal 'tail' (as well other non-tail sites) of histone H3 are critical for multiple DNA-templated processes. Notably, H3K27 is the target of methylation by Polycomb Repressive Complex 2 (PRC2) to modulate gene transcription (and in some cases, acetylation, brought about by distinct enzyme systems. The mono-, di-, and tri-methylation states of histone H3-K27 are associated with different functions in transcriptional control. Histone H3-K27 monomethylation (or acetylation) is often associated with active transcription of genes, such as differentiation genes, that are poised for transcription (Cui et al. "Chromatin Signatures in Multipotent Human Hematopoietic Stem Cells Indicate the Fate of Bivalent Genes During Differentiation, *Cell Stem Cell* 4:80-93 (2009) and Barski et al., "High-Resolution Profiling of Histone Methylation in the Human Genome," *Cell* 129:823-37 (2007)). In contrast, tri-methylation of histone H3-K27 is largely associated with either transcriptionally repressed genes or genes that are poised for transcription when histone H3-K4 trimethylation is in cis (Cui et al. "Chromatin Signatures in Multipotent Human Hematopoietic Stem Cells Indicate the Fate of Bivalent Genes During Differentiation, *Cell Stem Cell* 4:80-93 (2009); Kirmizis et al. "Silencing of Human Polycomb Target Genes is Associated with Methylation of Histone H3 Lys 27," *Genes Dev* 18:1592-1605 (2007); Bernstein et al. "A Bivalent Chromatin Structure Marks Key Developmental Genes in Embryonic Stem Cells," *Cell* 125:315-26 (2006).

The overexpression of genes in the PRC2 complex has been associated with a number of cancers, including, for example, metastatic prostate cancer (Crea et al., "Pharmacologic Disruption of Polycomb Repressive Complex 2 Inhibits Tumorigenicity and Tumor Progression in Prostate Cancer," *Mol. Cancer* 10:40 (2011), breast cancer (Holm et al., "Global H3K27 Trimethylation and EZH2 Abundance in Breast Cancer Tumor Subtypes," *Mol. Oncol*. [PMID:22766277 Epub] (June 2012)), bladder cancer (Raman et al., "Increased Expression of the Polycomb Group Gene, EZH2, in Transitional Cell Carcinoma of the Bladder," *Clin. Cancer Res.* 11:8570-6 (2005)), gastric cancer (Matsukawa et al., "Expression of the Enhancer of Zeste Homolog 2 is Correlated with Poor Prognosis in Human Gastric Cancer," *Cancer Sci.* 97:484-91 (2006)), melanoma, and lymphoma (McCabe et al., "Mutation of A677 in Histone Methyltransferase EZH2 in Human B-cell Lymphoma Promotes Hypertrimethylation of Histone H3 on Lysine 27 (H3K27)," *Proc. Nat'l Acad. Sci. USA* 109(8):2989-94 (2012)). The overexpression of polycomb genes and subsequent increase in PRC2 complex activity that has been reported in cancer is predicted to increase the trimethylated state of histone H3-K27 and thus result in transcriptional repression of several tumor suppressor genes (Crea et al., "EZH2 Inhibition: Targeting the Crossroad of Tumor Invasion and Angiogenesis," *Cancer Metastasis Rev.* doi:10.1007/s10555-012-9387-3 (2012). Accordingly, agents capable of disrupting this cascade of events would be therapeutically useful for the treatment of cancer.

SUMMARY OF THE INVENTION

A first aspect of the present invention relates to an isolated peptide comprising an amino acid sequence of XAARMSX-PXXG (SEQ ID NO:1), wherein X is any amino acid residue.

Another aspect of the present invention relates to a method of treating a subject having cancer that involves selecting a subject having cancer and administering an isolated peptide comprising an amino acid sequence of XAARMSXPXXG (SEQ ID NO:1), wherein X is any amino acid residue, to the subject under conditions effective to treat the cancer.

Recent exome sequencing studies of Pediatric Diffuse Pontine Gliomas (DIPG) and Glioblastoma Multiforme (GBM) identified the missense mutation K27M in genes encoding histone H3.3 (H3F3A) and H3.1 (HIST3H1B). The heterozygous nature of these mutations suggests that they promote gliomagenesis through a gain-of-function mechanism that is not understood. As shown herein, expression of H3.1 or H3.3 transgenes with the K27M mutation leads to a striking reduction of H3K27me3 on the non-mutated H3 both within the same nucleosome and on nearby nucleosomes. This reduction is specific for the methionine substitution at position 27 as transgenes encoding K27R or K27Q do not cause lower K27me3 levels. The Polycomb Repressive Complex 2 (PRC2) shows decreased methyltransferase activity on nucleosome templates containing H3K27M. These and other data led to the discovery of isolated peptides derived from H3K27M that function as potent PRC2 inhibitors. To date, few, if any, inhibitors for PRC2 exist, despite active investigation by academic, biotech, and pharmaceutical entities into the link between PRC2 activity, H3K27 methylation and the variety of human cancers cited above.

BRIEF DESCRIPTION OF THE DRAWINGS

FIG. 1A shows immunoblots of acid-extracted histones from DIPGs with wildtype H3 or the H3K27M mutation in H3F3A or HIST3H1B. These blots show that diffuse pontine gliomas with H3K27M mutation have decreased H3K27me3 levels. FIG. 1B are immunoblots of whole cell extract from HEK283T cells that stably express epitope-tagged histone H3.3. Expression of H3K27M causes reduction in H3K27me3 levels in HEK293T cells. FIG. 1C are immunoblots of FLAG-immunoprecipitated mononucleosomes from micrococcal nuclease digested HEK293T cell nuclei. As shown, mononucleosomes containing H3K27M have reduced H3K27me3. FIG. 1D are immunoblots of FLAG-immunoprecipitated oligonucleosomes (mean 4-6 nucleosomes) from micrococcal nuclease digested HEK293T cell nuclei. Oligonucleosomes containing H3K27M also have reduced H3K27me3.

FIG. 2A is a silver stained gel of PRC2 used for in vitro histone methyltransferase (HMT) reactions. FIG. 2B is a coomassie stained gel of purified mono- or oligo-nucleosomes used for in vitro PRC2 histone methyltransferase reactions. FIG. 2C shows that H3K27M-containing chromatin templates are poor substrates for PRC2-dependent methylation. Shown is a fluorograph of in vitro HMT assay with purified PRC2 and chromatin templates show in FIGS. 2A and 2B. The decrease in PRC2-dependent methylation is specific for H3K27M chromatin as shown in the fluorograph of FIG. 2D. Fluorograph from in vitro HMT assay with purified mononucleosomes containing H3K27M, K27R, K27A or K27Q and PRC2.

FIGS. 3A and 3B show titration of various H3 peptides (18-37) into in vitro HMT assay with PRC2 and purified wildtype (FIG. 3A) or H3K27M-containing mononucleosomes (FIG. 3B). FIG. 3C shows the quantitation of HMT assays on purified mononucleosome substrates. Unmodified (18-37), K27ac or K27M missense mutations in H3F3A and HIST3H1B were verified by DNA sequencing. As shown in FIG. 3D, increased H3K27ac/ H3K27me3 peptide ratio does not affect allosteric activation of PRC2 by H3K27me3 peptide. An increased ratio of H3K27M/H3K27me3 peptide ratio decreases H3K27me3-dependent allosteric activation or PRC2 as shown in FIG. 3E. FIG. 3F shows inhibition of PRC2 activity by titration of H3K27M, but not H3K27ac peptides.

FIG. 4B is a double-reciprocal Lineweaver-Burke plot corresponding to the data in FIG. 4A.

FIG. 5A are immunoblots of whole-cell extract from lentivirus-transduced 293T cells expressing the indicated H3.3 transgenes. FIG. 5B shows a fluorography of PRC2 methyltransferase reactions with reconstituted nucleosomes containing recombinant human histones H3, H2B, H2A and H4. Reactions also contain 100 µM H3 peptides (18-37) containing K27acetyl, K27Ile, K27Met, K27Nle, or K27Leu. Quantification of PRC2 methyltransferase activity in the presence of 50 µM of H3 peptides (18 to 37) containing K27acetyl, K27Leu, K27Ile, K27Met, or K27Nle is shown in the graph of FIG. 5C. Error bars represent standard deviation of three repeats. FIG. 5D is a graph showing the $IC_{50}$ measurement for methionine or norleucine substitution at K27. Titration reactions of H3.3K27M or K3.3K27Nle peptides with 70 ng PRC2 and 0.8 µg wild-type oligonucleosomes. Error bars represent the standard deviation of five repeats.

DETAILED DESCRIPTION OF THE INVENTION

Figures 1A, 1B, 1C, 1D:
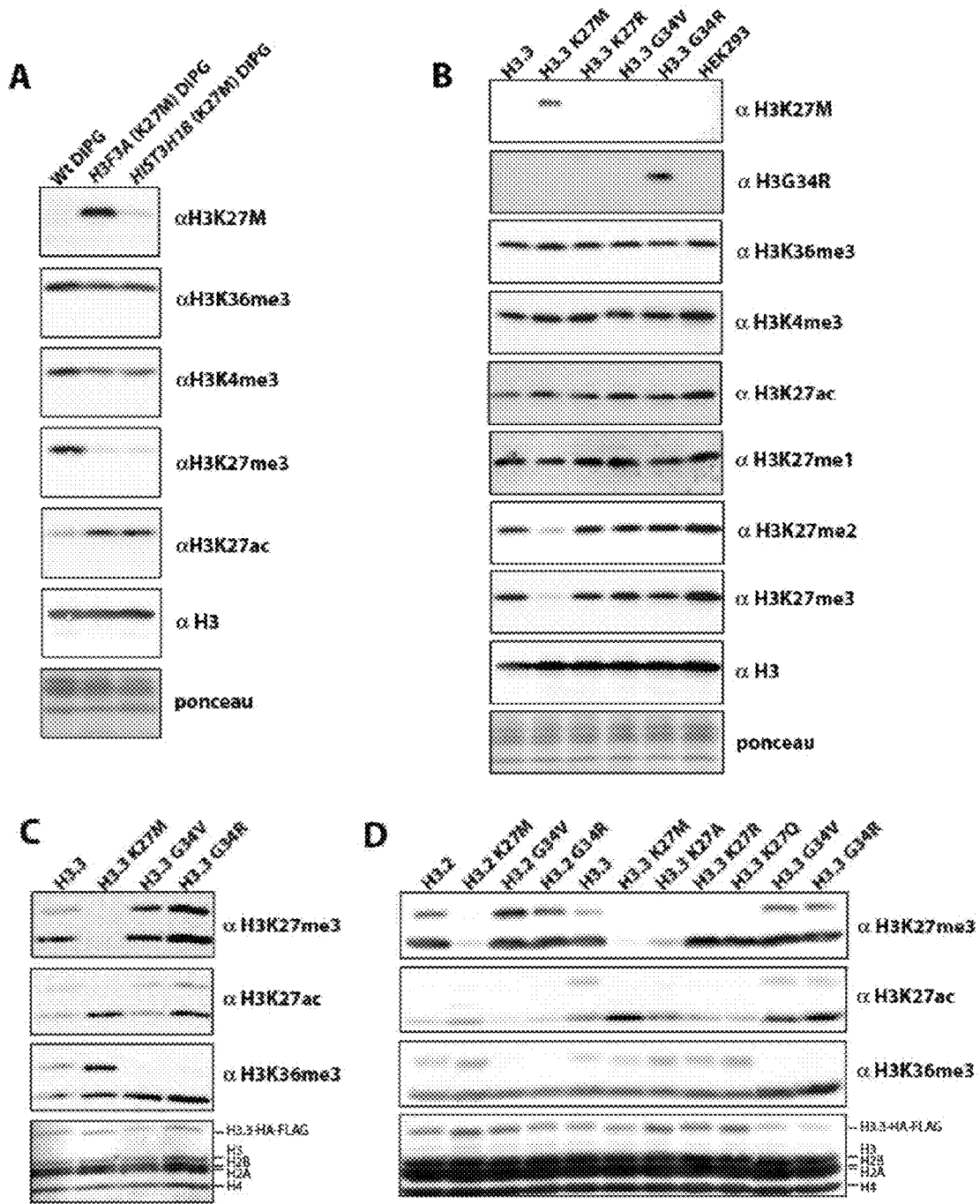
FIGS. 1A-1D show the decrease in H3K27me3 achieved with expression of H3K27M.

The present invention relates generally to novel peptide inhibitors of Polycomb Repressive Complex 2 (PRC2) methyltransferase activity and methods of using these peptide inhibitors for the treatment of cancers and other conditions associated with aberrant methyltransferase activity of the PRC2 complex. As described herein, isolated peptides derived from mutant histone H3.1 and H3.3 proteins, containing a lysine (K) to methionine (M) substitution at amino acid position 27 of each full-length protein sequence are potent inhibitors of PRC2 methyltransferase activity. The core amino acid sequence of the aforementioned isolated peptides that is responsible for PRC2 inhibition is AARMS (SEQ ID NO: 1). Accordingly, a first aspect of the present invention relates to an isolated peptide comprising the amino acid sequence AARMS (SEQ ID NO:1), which corresponds to amino acid residues 24-28 of the K27M mutant sequence of H3.1 (SEQ ID NO: 2) or H3.3 (SEQ ID NO: 3) as shown below.

```
H3.1 (SEQ ID NO: 2)
  1  artkqtarkstggkaprkqlatkaarmsapatggvkkphryrpgtvalreirryqkste 60  llirklpfqrlvreiaqdfktdlrfqssavmalqeaceaylvglfedtnlcaihakrvti 120  mpkdiqlarrirgera H3.3 (SEQ ID NO: 3)
  1  artkqtarkstggkaprkqlatkaarmsapstggvkkphryrpgtvalreirryqkste 60  llirklpfqrlvreiaqdfktdlrfqsaaigalqeaseaylvglfedtnlcaihakrvti 120  mpkdiqlarrirgera
```

Isolated peptides derived from SEQ ID NOs: 2 or 3 containing the AARMS inhibitory sequence can vary in sequence length. In one embodiment, the isolated peptide of the present invention comprises a total length of less than 100 amino acid residues. In another embodiment the isolated peptide of the present invention comprises a length of less than 75 amino acid residues. In another embodiment, the isolated peptide of the present invention is 50 amino acids or less. Typically, the isolated peptide of the present invention ranges between 5 and 100 amino acid residues in length, more preferably the isolated peptide ranges between 10 and 75 amino acid residues in length, more preferably the isolated peptide ranges between 10 and 50 amino acid residues in length. For example, the isolated peptide of the present invention can be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues in length.

Variants of the isolated peptides derived from SEQ ID NOs: 2 or 3 are also encompassed by the present invention. Suitable variant peptides include those peptides having one or more amino acid substitutions that retain the ability to inhibit PRC2 methyltransferase activity. More specifically, the present invention encompasses any isolated variant peptides that inhibit PRC2 mediate H3K27 tri-methylation (H3K27me3). Inhibitory functionality of a variant peptide can readily be assessed using various assays, including, for example and without limitation, an in vitro H3K27 methyltransferase assay as described in the Examples herein.

A variant peptide of the present invention may contain one or more amino acid residue additions, deletions, or substitutions. An isolated variant peptide of the present invention retains at least about 30-50% sequence identity to the amino acid sequence of H3.1 or H3.3 from which it is derived from. Preferably, variant peptides retain at least 60-70% or 70-80% sequence identity to the amino acid sequence of H3.1 or H3.3. More preferably, variant peptides retain at least 80-90% sequence identity to the amino acid sequence H3.1 or H3.3. Most preferably, variant peptides of the present invention retain 90-95% or 95-99% sequence identity to the amino acid sequence of the H3.1 or H3.3 which it is derived from.

When a variant peptide of the present invention comprises amino acid substitutions, such substitutions preferably comprise conservative natural or non-natural amino acid substitutions. Conservative amino acid substitutions may include synonymous amino acid residues within a group which have sufficiently similar physicochemical properties, so that a substitution between members of the group will preserve the biological activity of the molecule (see e.g. Grantham, R., "Amino Acid Difference Formula to Help Explain Protein Evolution," *Science* 185: 862-864 (1974), which is hereby incorporated by reference in its entirety). It is evident that amino acids may also be inserted and/or deleted in the above-defined sequences without altering their function, particularly if the insertions and/or deletions only involve a few amino acids, e.g. less than 5 to 10, and preferably less than 2 to 5, and do not remove or displace amino acids which are critical to functional activity (i.e., the core AARMS sequence). Synonymous amino acid residues are identified in Table 1 below. Other conservative interchanges include those within the aliphatic group aspartate and glutamate; within the amide group asparagine and glutamine; within the hydroxyl group serine and threonine; within the chromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

TABLE 1

Preferred Groups of Synonymous Amino Acid Residues

| Amino Acid | Synonymous Residue |
|---|---|
| Ser | Thr, Gly, Asn |
| Arg | Gln, Lys, Glu, His |
| Leu | Ile, Phe, Tyr, Met, Val |
| Pro | Gly, Ala, (Thr) |
| Thr | Pro, Ser, Ala, Gly, His, Gln |
| Ala | Gly, Thr, Pro |
| Val | Met, Tyr, Phe, Ile, Leu |
| Gly | Ala, (Thr), Pro, Ser |
| Ile | Met, Tyr, Phe, Val, Leu |
| Phe | Trp, Met, Tyr, Ile, Val, Leu |
| Tyr | Trp, Met, Phe, Ile, Val, Leu |
| Cys | Ser, Thr |
| His | Glu, Lys, Gln, Thr, Arg |
| Gln | Glu, Lys, Asn, His, (Thr), Arg |
| Asn | Gln, Asp, Ser |
| Lys | Glu, Gln, His, Arg |
| Asp | Glu, Asn |
| Glu | Asp, Lys, Asn, Gln, His, Arg |
| Met | Phe, Ile, Val, Leu |
| Trp | Trp |

In one embodiment of this aspect of the present invention, the isolated peptide comprises an amino acid sequence of XAARMSXPXXG (SEQ ID NO: 4), where, X at positions 1, 7, 9, and 10 is any amino acid residue. Alternatively, X at position 1 of SEQ ID NO: 4 comprises a K or arginine (R) residue, X at position 7 of SEQ ID NO: 4 comprises an alanine (A) or serine (S) residue, and X at positions 9 and 10 of SEQ ID NO: 4 comprises an S, A, or threonine (T) residue. Sequences of isolated peptides encompassed by SEQ ID NO: 4 are identified in Table 2 below by SEQ ID NO.

TABLE 2

Exemplary Isolated Peptide Sequences

| Isolated Peptide Sequence | SEQ ID NO: |
|---|---|
| KAARMSAPSTG | 5 |
| KAARMSAPTTG | 6 |
| KAARMSAPATG | 7 |
| RAARMSAPSTG | 8 |
| RAARMSAPTTG | 9 |
| RAARMSAPATG | 10 |
| KAARMSSPSTG | 11 |
| KAARMSSPTTG | 12 |
| KAARMSSPATG | 13 |
| RAARMSSPSTG | 14 |
| RAARMSSPTTG | 15 |
| RAARMSSPATG | 16 |
| KAARMSAPSSG | 17 |
| KAARMSAPTSG | 18 |
| KAARMSAPASG | 19 |
| RAARMSAPSSG | 20 |
| RAARMSAPTSG | 21 |
| RAARMSAPASG | 22 |
| KAARMSSPSSG | 23 |
| KAARMSSPTSG | 24 |
| KAARMSSPASG | 25 |
| RAARMSSPSSG | 26 |
| RAARMSSPTSG | 27 |
| RAARMSSPASG | 28 |
| KAARMSAPSAG | 29 |
| KAARMSAPTAG | 30 |
| KAARMSAPAAG | 31 |
| RAARMSAPSAG | 32 |
| RAARMSAPTAG | 33 |
| RAARMSAPAAG | 34 |
| KAARMSSPSAG | 35 |
| KAARMSSPTAG | 36 |
| KAARMSSPAAG | 37 |
| RAARMSSPSAG | 38 |
| RAARMSSPTAG | 39 |
| RAARMSSPAAG | 40 |

In another embodiment of the present invention, the isolated peptide comprises an amino acid sequence of TXAARMSXPXXGGVK (SEQ ID NO: 41), where X at positions 2, 8, 10, and 11 comprises any amino acid residue. Alternatively, X at position 2 of SEQ ID NO: 41 comprises a K or R residue, X at position 8 of SEQ ID NO: 41 comprises an A or S residue, and X at positions 10 and 11 of SEQ ID NO: 41 comprises a S, A, or T residue. As can be appreciated by one of skill in the art, isolated peptides in accordance with this embodiment of the present invention comprise any one of the amino acid sequences shown in Table 2 above flanked by a T residue at the amino-terminus and GVK residues at the carboxy-terminus. Exemplary isolated peptides of the present invention comprise, without limitation, the amino acid sequence of TKAARMSAPATGGVK (SEQ ID NO: 42) or TKAARMSAPATGGVK (SEQ ID NO: 43). The present invention further relates to isolated nucleic acid molecules encoding the peptides of the present invention as described in more detail infra.

In another embodiment of the present invention, the isolated peptide comprises an amino acid sequence of KQLATXAARMSXPXXGGVKK (SEQ ID NO: 44), X at positions 6, 12, 14, and 15 comprises any amino acid residue. Alternatively, X at position 6 of SEQ ID NO: 44 comprises a K or R residue, X at position 12 of SEQ ID NO: 44 comprises an A or S residue, and X at positions 14 and 15 of SEQ ID NO: 44 comprises a S, A, or T residue. As can be appreciated by one of skill in the art, isolated peptides in accordance with this embodiment of the present invention comprise any one of the amino acid sequences shown in Table 2 above, flanked by KQLAT residues at the amino-terminus and GVKK residues at the carboxy-terminus. Exemplary isolated peptides of the present invention comprise, without limitation, the amino acid sequence of KQLATKAARMSAPATGGVKK (SEQ ID NO: 45) or KQLATKAARMSAPSTGGVKK (SEQ ID NO: 46). The present invention further relates to isolated nucleic acid molecules encoding the peptides of the present invention as described in more detail infra.

The isolated peptides of the present invention may be composed exclusively of L-amino acids, D-amino acids, or any combination thereof. Peptides comprising D-amino acids are advantageous because they are less susceptible to degradation, enter cells as easily as an L-amino acid peptide, are easy to synthesize, and in some cases are less antigenic. A peptide of the present invention comprising D-amino acids preferably comprises a D-retro-inverso-peptide sequence corresponding to its L-amino peptide sequence counterpart. A "retro-inverso sequence" is an isomer of a linear peptide sequence in which the direction of the sequence is reversed and the chirality of each amino acid residue is inverted (see e.g., Jameson et al., "A Rationally Designed CD4 Analogue Inhibits Experimental Allergic Encephalomeylitis," *Nature* 368:744-746 (1994) and Brady et al., "Drug Design. Reflections on a Peptide," *Nature* 368:692-693 (1994), which are hereby incorporated by reference in their entirety). The advantage of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence or peptide according to the present invention may be converted into an D-retro-inverso sequence or peptide by synthesizing a reverse of the sequence or peptide for the corresponding native L-amino acid sequence or peptide.

The isolated peptides of the present invention are preferably acetylated at the N-terminus and amidated at the carboxy terminus to increase cell permeability and enhance peptide stability. Methods of N-terminal acetylation and C-terminal amidation of synthetic peptides are well known in the art.

Another aspect of the present invention relates to fusion peptides comprising the isolated peptide described herein and a targeting moiety that is coupled to the isolated peptide. Suitable targeting moieties include cell specific targeting moieties, cell-penetrating moieties, and intracellular localization or trafficking moieties. One or more targeting moieties can be coupled to the amino and/or carboxy termini of the isolated peptide of the invention.

In one embodiment, the targeting moiety comprises a signal peptide sequence or antibody capable of targeting the isolated peptide of the present invention to a particular tissue or cell type. The signaling peptide can include at least a portion of a ligand binding protein. Suitable ligand binding proteins include high-affinity antibody fragments (e.g., Fab, Fab' and F(ab')$_2$, single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the isolated peptide is delivered intravenously or otherwise introduced into blood or lymph, the peptide is delivered and taken up by the targeted cell. Targeting ligands suitable for directing an isolated peptide of the invention to a cancerous or leukemic cell include, without limitation anti-CD64 antibodies (suitable for targeting acute myeloid leukemia blasts), GM-CSF (acute myeloid leukemia), anti-GD2 antibody (metastatic melanoma), anti-CD22 antibody (hairy cell leukemia), IL-2 (T-cell lymphoma), anti-Her-2/new scFv antibody (Her-2/neu expressing cancer, e.g., breast cancer), transferrin, anti-CD25 antibodies, TGFα, folic acid, anti-CEA antibodies (CEA expressing colon cancer), anti-EpCAM scFv antibodies, VEGF, galactose alpha 1,3-galactose, MOv19 scFv antibodies, and anti-CD20 antibodies (lymphoma) (see Lu et al., "Issues Related to Targeted Delivery of Proteins and Peptides," *AAPS Journal* 8(3):E466-E478 (2006), which is hereby incorporated by reference in its entirety).

In another embodiment, the targeting moiety comprises a sequence that directs cell uptake of the peptide. For example, the targeting moiety can be derived from a known membrane-translocating sequence, such as the sequence for human immunodeficiency virus (HIV)-1 trans-activator of transcription (TAT) protein (see e.g., U.S. Pat. No. 5,804,604 to Frankel et al, and U.S. Pat. No. 5,674,980 to Frankel et al., which are hereby incorporated by reference in their entirety). An isolated peptide of the present invention may be coupled to the 86 amino acid residue TAT protein or a fragment thereof. Preferably, a functionally effective fragment or portion of a TAT protein that has fewer than 86 amino acids, exhibits uptake into cells, and optionally uptake into the cell nucleus is utilized. In one embodiment, the TAT peptide comprises amino acid residues 48-57, e.g. NH$_2$-GRKKRRQRRR-COOH (SEQ ID NO: 47), a generic TAT sequence NH$_2$-X$_n$-RKKRRQRRR-X$_n$-COOH (SEQ ID NO: 48), or a D-retro-inverso peptide having the sequence NH$_2$-X$_n$-RRRQRRKKR-X$_n$-COOH (SEQ ID NO: 49). A TAT peptide that includes the region that mediates entry and uptake into cells can be further defined using known techniques (see e.g., Frankel et al, "Activity of Synthetic Peptides from the Tat Protein of Human Immunodeficiency Virus Type-1," *Proc. Natl. Acad. Sci. USA* 86: 7397-7401 (1989), which is hereby incorporated by reference in its entirety).

The TAT sequence may be coupled to the N-terminal or the C-terminal end of the isolated peptide of the present invention. A hinge of two proline residues may be added between the TAT and the isolated peptide of the present invention to create a fusion peptide. Alternatively, the TAT sequence can be linked to the isolated peptide of the present invention using other suitable linker sequences, such as, glycine-rich (e.g. $G_{3-5}$) or serine-rich (e.g., GSG, GSGS (SEQ ID NO: 50), GSGSG (SEQ ID NO: 51), $GS_NG$) linker sequences, or flexible immunoglobulin linkers as disclosed in U.S. Pat. No. 5,516,637 to Huang et al, which is hereby incorporated by reference in its entirety.

The TAT targeting moiety can be a single (i.e., continuous) amino acid sequence present in the TAT sequence. Alternatively it can be two or more amino acid sequences, which are present in TAT protein, but are not contiguous in the naturally-occurring TAT protein. Modifications to TAT protein and fragments thereof designed to modulate intracellular localization and/or enhance membrane solubility are further described in U.S. Pat. No. 5,804,604 to Frankel et al, and U.S. Pat. No. 5,674,980 to Frankel et al., which are hereby incorporated by reference in their entirety. TAT protein can be obtained from naturally-occurring sources or can be produced using genetic engineering techniques or chemical synthesis.

Another suitable targeting moiety useful for promoting the cellular uptake of an isolated peptide of the present invention comprises a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem* 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of an isolated peptide of the present invention is an "importation competent" signal peptide as disclosed by U.S. Pat. No. 6,043,339 to Lin et al., which is hereby incorporated by reference in its entirety. An importation competent signal peptide is generally about 10 to about 50 amino acid residues in length, typically hydrophobic residues, which render the peptide capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety).

Another suitable targeting sequence or moiety is a transport peptide that directs intracellular compartmentalization of the isolated peptide once it is internalized by a target cell or tissue. For example, to achieve nuclear localization, the isolated peptide of the present invention is coupled to a nuclear localization transport signal. Suitable nuclear transport peptide sequences are known in the art, including the nuclear transport peptide PPKKKRKV (SEQ ID NO: 52). Other nuclear localization transport signals include, for example, the nuclear localization sequence of acidic fibroblast growth factor, the nuclear localization sequence of the transcription factor NF-KB p50 (U.S. Pat. No. 6,043,339 to Lin et al., which is hereby incorporated by reference in its entirety), and the intracellular trafficking sequence derived from the Herpesvirus structural VP22 protein (WO 97/05265 to O'Hare and Elliott and O'Hare, "Intracellular Trafficking and Protein Delivery by a Herpesvirus Structural Protein," *Cell* 88: 223-233 (1997), which are hereby incorporated by reference in their entirety.

The targeting moiety can be coupled to the isolated peptide of the present invention by chemical coupling in any suitable manner known in the art. In one embodiment, the chemical cross-linking method is a non-specific method, i.e. the point of coupling is not directed to any particular site on the transport or cargo peptide or polypeptide. Alternatively, the targeting moiety can be directly coupled to the isolated peptide of the present invention via a functional group (e.g., cysteine residue or primary amine), found only once or a few times in one or both of the targeting moiety and cargo peptide to be cross-linked.

Coupling of the two constituents can be accomplished via a coupling or conjugating agent. There are several intermolecular cross-linking reagents which can be utilized, e.g., J-succinimidyl 3-(2-pyridyldithio) propionate (SPDP) or N,N'-(1,3-phenylene)bismaleimide (both of which are highly specific for sulfhydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other cross-linking reagents useful for this purpose include, without limitation, p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine). Heterobifunctional cross-linking agents having two different functional groups, e.g., amine- and thiol-reactive groups, that will cross-link two proteins having free amines and thiols, respectively, are also suitable cross-linking agents. Examples of heterobifunctional cross-linking agents include succinimidyl 4-(N-maleimidomethyl) cyclohexane-1-carboxylate, m-maleimidobenzoyl-N-hydroxysuccinimide ester, and succinimide 4-(p-maleimidophenyl) butyrate. The succinimidyl group of these cross-linkers reacts with a primary amine, and the thiol-reactive maleimide forms a covalent bond with the thiol of a cysteine residue.

In one embodiment of the present invention, a cross-linking reagent that forms a cleavable covalent bond (e.g., disulfide bond) under cellular conditions is preferentially utilized. Exemplary cross-linking agents that form cleavable bonds include, without limitation, Traut's reagent, dithiobis (succinimidylpropionate), and N-succinimidyl 3-(2-pyridyldithio) propionate. The use of a cleavable cross-linking reagent permits the cargo moiety (i.e., the PCR2 inhibitory peptide) to separate from the transport polypeptide after delivery into the target cell.

The isolated peptides of the present invention may be prepared using standard methods of synthesis known in the art, including solid phase peptide synthesis (Fmoc or Boc strategies) or solution phase peptide synthesis. Alternatively, peptides of the present invention may be prepared using recombinant expression systems as described below.

Generally, the use of recombinant expression systems involves inserting the nucleic acid molecule encoding the amino acid sequence of the desired peptide into an expression system to which the molecule is heterologous (i.e., not normally present). Isolated nucleic acid molecules encoding the peptides of the present invention can be derived from the nucleotide sequences encoding H3.1 (SEQ ID NO: 53) and H3.3 (SEQ ID NO: 54) shown below.

ING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be

```
mRNA H3.1 SEQ ID NO: 53 (NCBI Ref. Seq. No. NM_003529)
    1   atggctcgca ctaagcaaac tgctcggaag tctactggtg gcaaggcgcc acgcaaacag 61   ttggccacta aggcagcccg caaaagcgct ccggccaccg gcggcgtgaa aaagccccac 121   cgctaccggc cgggcaccgt ggctctgcgc gagatccgcc gttatcagaa gtccactgaa 181   ctgcttattc gtaaactacc tttccagcgc ctggtgcgcg agattgcgca ggactttaaa 241   acagacctgc gtttccagag ctccgctgtg atggctctgc aggaggcgtg cgaggcctac 301   ttggtagggc tatttgagga cactaacctg tgcgccatcc acgccaagcg cgtcactatc 361   atgcccaagg acatccagct cgcccgccgc atccgcggag agagggcgtg attactgtgg 421   tctctctgac ggtccaagca aaggctcttt tcagagccac cacctttc mRNA H3.3 SEQ ID NO: 54 (NCBI Ref. Seq. No. NM_002107)
    1   gtcagccatc tttcaattgt gttcgcagcc gccgccgcgc cgccgtcgct ctccaacgcc 61   agcgccgcct ctcgctcgcc gagctccagc cgaaggagaa gggggtaag taaggaggtc 121   tctgtaccat ggctcgtaca aagcagactg cccgcaaatc gaccggtggt aaagcaccca 181   ggaagcaact ggctacaaaa gccgctcgca agagtgcgcc ctctactgga ggggtgaaga 241   aacctcatcg ttacaggcct ggtactgtgg cgctccgtga aattagacgt tatcagaagt 301   ccactgaact tctgattcgc aaacttccct tccagcgtct ggtgcgagaa attgctcagg 361   actttaaaac agatctgcgc ttccagagcg cagctatcgg tgctttgcag gaggcaagtg 421   aggcctatct ggttggcctt tttgaagaca ccaacctgtg tgctatccat gccaaacgtg 481   taacaattat gccaaaagac atccagctag cacgccgcat acgtggagaa cgtgcttaag 541   aatccactat gatgggaaac atttcattct caaaaaaaaa aaaaaaaatt tctcttcttc 601   ctgttattgg tagttctgaa cgttagatat ttttttttcca tggggtcaaa aggtacctaa 661   gtatatgatt gcgagtggaa aaataggga cagaaatcag gtattggcag tttttccatt 721   ttcatttgtg tgtgaatttt taatataaat gcggagacgt aaagcattaa tgcaagttaa 781   aatgtttcag tgaacaagtt tcagcggttc aactttataa taattataaa taaacctgtt 841   aaatttttct ggacaatgcc agcatttgga ttttttaaa acaagtaaat ttcttattga 901   tggcaactaa atggtgtttg tagcattttt atcatacagt agattccatc cattcactat 961   acttttctaa ctgagttgtc ctacatgcaa gtacatgttt ttaatgttgt ctgtcttctg 1021   tgctgttcct gtaagtttgc tattaaaata cattaaacta taaaaaaaaa aaaaaa
```

One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONincorporated into the nucleic acid construct to maximize peptide production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in E. coli, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated peptide of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety. Once the nucleic acid molecule encoding the peptide has been cloned into an expression vector, it is incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Recombinantly produced peptides of the invention can be purified by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Another aspect of the present invention relates to pharmaceutical compositions containing the isolated peptides or fusion peptides of the present invention. The pharmaceutical compositions may further comprise a pharmaceutically acceptable excipient, carrier, buffer, stabilizer or other material well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, nasal, intramuscular, intraperitoneal, patch route, or other.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or direct injection at a tumor site, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Administration is preferably carried out to achieve delivery of a therapeutically effective amount of the PRC2 inhibitory peptide. As used herein, a "therapeutically effective amount" is the amount sufficient to show benefit to the individual (i.e., a slowing or inhibition of cancer progression). The actual amount administered, and rate and time-course of administration, will depend on the nature and severity of cancer being treated. Techniques for formulation and administration of the isolated peptides of the present invention may be found in references well known to one of ordinary skill in the art, such as Remington's "The Science and Practice of Pharmacy," 21st ed., Lippincott Williams & Wilkins 2005.

The pharmaceutical compositions of the present invention can be formulated for parenteral administration by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for reconstitution before use with a suitable vehicle, e.g., sterile pyrogen-free water.

In addition to the formulations described previously, the pharmaceutical compositions of the present invention may also be formulated as a depot preparation. Such long acting formulations may be administered by implantation (for example, subcutaneously or intramuscularly or by intramuscular injection). Thus, for example, the pharmaceutical composition may be formulated with suitable polymeric or hydrophobic materials (for example as an emulsion in an acceptable oil) or ion exchange resins, or as sparingly soluble derivatives (for example, as a sparingly soluble salt). Additionally, the pharmaceutical composition of the present invention may be delivered using a sustained-release system, such as semipermeable matrices of solid hydrophobic polymers containing the composition. Various sustained-release materials have been established and are well known by those skilled in the art. Sustained-release capsules may, depending on their chemical nature, release pharmaceutical composition for a few weeks or up to over 100 days. Depending on the chemical nature and the biological stability of the therapeutic composition, additional strategies for protein stabilization may be employed.

Another aspect of the present invention relates to a method of treating a subject having cancer that involves selecting a subject having cancer and administering to the selected subject, an isolated peptide of the present invention under conditions effective to treat the cancer. Suitable isolated peptides of the present invention include peptides comprising the amino acid sequence of SEQ ID NO: 4 (XAARMSXPXXG), SEQ ID NO: 41 (TXAARMSXPXXGGVK), or SEQ ID NO: 44 (KQLATXAARMSXPXXGGVKK) as described supra.

As used herein, a "subject" is any animal, preferably a mammal, more preferably a human.

Since increased histone methylation via PRC2 complex activity has been associated with certain cancers, a method for treating these types of cancer in a subject involves administering to the subject a therapeutically effective amount of an isolated peptide of the present invention that inhibits methyltransferase activity, or restores methyltransferase activity to roughly its level in counterpart normal cells. In accordance with one embodiment of this aspect of the present invention, the method of treating cancer in a subject involves administering to the subject having cancer a therapeutically effective amount of an isolated peptide of the present invention that inhibits conversion of unmethylated H3-K27 to monomethylated H3-K27 (H3-K27me1). In another embodiment of the present invention, the method of treating a subject having cancer comprises administering to the subject in need thereof a therapeutically effective amount of an isolated peptide of the present invention that inhibits conversion of H3-K27me1 to dimethylated H3-K27 (H3-K27me2). In another embodiment of the present invention, the method of treating a subject having cancer involves administering to the subject a therapeutically effective amount of an isolated peptide of the present invention that inhibits conversion of H3-K27me2 to trimethylated H3-K27 (H3-K27me3). In another embodiment of the present invention, the method of treating a subject having cancer involves administering to the subject a therapeutically effective amount of a compound that inhibits both conversion of H3-K27me1 to H3-K27me2 and conversion of H3-K27me2 to H3-K27me3. It is important to note that a disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation.

Subjects particularly suitable for treatment in accordance with the methods of the present invention have a cancer, leukemia, or lymphoma that involves or is associated with aberrant PRC2 methyltransferase activity. Cancers known to involve aberrant PRC2 methyltransferase activity include, without limitation, leukemia (e.g., mixed-lineage leukemia, acute myeloid leukemia, and chronic myelomonocytic leukemia), lymphoma (e.g., follicular lymphoma and diffuse large B-cell lymphoma (DLBCL)), breast cancer, melanoma, bladder cancer, gastric cancer, endometrial cancer, prostate cancer, Ewing sarcoma, and non-small cell lung cancer. Clinicians can readily identify whether a subject has a cancer involving aberrant PRC2 methyltransferase activity by assaying PRC2 activity or H3K27 methylation levels in a tumor or cancer cell sample using methods well known in the art and described herein. Alternatively, suitable subjects can be identified with genetic screening for mutations in PRC2 proteins that are linked to increased PRC2 activity and cancer, such as the Y641 mutation in EZH2 (Yap et al., "Somatic Mutations at EZH2 Y641 Act Dominantly Through a Mechanism of Selectively Altered PRC2 Catalytic Activity, to Increase H3K27 Trimethylation," *Blood* 117(8):2451 (2011), which is hereby incorporated by reference in its entirety) or the A677 mutation in EZH2 (McCabe et al., "Mutation of A677 in Histone Methyltransferase EZH2 in Human B-Cell Lymphoma Promotes Hypertrimethylation of Histone H3 on Lysine 27 (H3K27)," *Proc. Nat'l. Acad. Sci. USA* 109(8):2989-94 (2012), which is hereby incorporated by reference in its entirety).

In accordance with this aspect of the present invention, the isolated PRC2 inhibitory peptides of the invention, or a pharmaceutical composition containing the same, can be used in combination with another anti-cancer therapeutic agent to treat cancer. The additional anti-cancer therapeutic agent is typically an agent that is art-recognized as being useful to treat the particular cancer being treated. The additional agent also can be an agent that imparts a beneficial attribute to the therapeutic peptide composition (e.g., an agent that affects the viscosity of the composition).

The isolated peptides, including fusion peptides, of the present invention or pharmaceutical composition containing the same can be administered simultaneously or sequentially with the additional therapeutic agent. In one embodiment, the combination therapy is formulated into a single pharmaceutical composition to achieve simultaneous administration. Alternatively, separate compositions comprising the PRC2 inhibitory peptides and the one or more additional cancer therapy agent(s) can be co-administration.

Suitable anti-cancer therapeutics that can be administered in combination with the PRC2 inhibitory peptides of the present invention include, without limitation, an agent that affects histone modifications, such as an HDAC inhibitor, a chemotherapeutic (e.g., Cladribine, 5-FU, 6-Mercaptopurine, 6-TG, Abraxane™, Accutane®, Actinomycin-D, Adriamycin™, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda®. and Zanosar®); biologics (such as Alpha Interferon, *Bacillus* Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

As used herein, a "therapeutically effective amount" or "therapeutically effective dose" is the dose of one or more isolated PRC2 inhibitory peptide(s) that inhibits, totally or partially, the progression of the cancerous condition or alleviates, at least partially, one or more symptoms of the cancerous condition. The dosage of peptide that is therapeutically effective will depend upon the patient's size and gender, the cancer to be treated, the severity (i.e., stage) of cancer condition, and the result sought. In one embodiment, a therapeutically effective dose refers to that dosage of a PRC2 inhibitory peptide that results in amelioration of cancer symptoms in a patient. For a given patient, a therapeutically effective amount may be determined by methods known to those of skill in the art.

Toxicity and therapeutic efficacy of PRC2 inhibitory peptides can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from cell culture assays and animal studies can be used in formulating a range of dosage for use in humans. Dosage may also be guided by monitoring the inhibitory peptide's effect on pharmacodynamic markers of enzyme inhibition (e.g., histone methylation or target gene expression) in diseased or surrogate tissue. Cell culture or animal experiments can be used to determine the relationship between doses required for changes in pharmacodynamic markers, and doses required for therapeutic efficacy can be determined in cell culture or animal experiments or early stage clinical trials. A suitable dosage of a PRC2 inhibitory peptide lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition.

Dosage amount and interval may be adjusted individually to provide plasma levels of the active moiety which are sufficient to maintain the methyltransferase modulating effects, or minimal effective concentration (MEC) for the required period of time to achieve therapeutic efficacy. The MEC will vary for each inhibitory peptide but can be estimated from in vitro data and animal experiments. Dosages necessary to achieve the MEC will depend on individual characteristics and route of administration. However, high pressure liquid chromatography (HPLC) assays or bioassays can be used to determine plasma concentrations.

Dosage intervals can also be determined using the MEC value. In certain embodiments, PRC2 inhibitory peptides should be administered using a regimen which maintains plasma levels above the MEC for 10-90% of the time, preferably between 30-90% and most preferably between 50-90% until the desired therapeutic effect is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and the amount inhibitory peptide administered will, of course, be dependent on the subject being treated, on the subject's weight, the severity of the affliction, the manner of administration and the judgment of the prescribing physician.

Another aspect of the present invention relates to antibodies that immunospecifically-bind H3.3 and/or H3.1 proteins and peptides thereof containing the K27M mutation. Preferably these antibodies are generated using the isolated peptides of the present invention as immunogens.

As used herein, the term "antibody" is meant to include intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988), which are hereby incorporated by reference in their entirety).

Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with an isolated peptide of the present invention either in vivo or in vitro. Exemplary isolated peptides are described supra. In one embodiment of this aspect of the present invention, the antibody is raised against an isolated peptide comprising the amino acid sequence of AARMSAPSC (SEQ ID NO: 55) or AARMSAPAC (SEQ ID NO: 56).

Immunogenic carrier proteins can be conjugated to the isolated peptides of the present invention via sulfhydryl, amine, or carboxyl groups to enhance antibody production. Suitable carrier proteins include, without limitation, keyhole limpet hemocyanin, blue carrier protein (hemocyanin), maledimide-activated blue carrier protein, bovine serum albumin, cationized bovine serum albumin, ovalbumin and maledimide-activated ovalbumin. In addition to the carrier protein, adjuvants, e.g., Freund's adjuvant and alum-based adjuvants, can be administered with the isolated peptides of the present invention to further enhance antibody production.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Procedures for raising polyclonal antibodies are also well known. Typically, such antibodies can be raised by administering the isolated peptides of the present invention subcutaneously to rabbits (e.g., New Zealand white rabbits), goats, sheep, swine, or donkeys which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

Methodologies for the screening of antibodies that possess the desired specificity include, but are not limited to, enzyme-linked immunosorbent assay (ELISA), western blot, and other immunologically-mediated techniques known within the art.

The antibodies of the present invention may be used in cancer diagnostic and prognostic methods. The lysine to methionine mutation at amino acid residue 27 of H3 has been implicated in high grade pediatric gliomas, including supratentorial glioblastomas (GBM) and diffuse intrinsic pointine gliomas (DIPG) (see e.g., Schwartzentruber et al., "Driver Mutations in Histone H3.3 and Chromatin Remodelling Genes in Paediatric Glioblastoma," *Nature* 482(7384):226-31 (2012), which is hereby incorporated by reference in its entirety). The presence of this mutation has also been linked to reduced survival in DIPG (Khuong-Quang et al., "K27M Mutation in Histone H3.3 Defines Clinically and Biologically Distinct Subgroups of Pediatric Diffuse Intrinsic Pontine Gliomas," *Acta Neuroathol.* 124(3):439-47 (20120), which is hereby incorporated by reference in its entirety), and its detection can be used to determine a patient's treatment regimen (e.g., patients with the K27M mutation may be started on a more aggressive treatment regimen early during the course of the disease).

Accordingly, another aspect of the present invention relates to a method of diagnosing or prognosing a subject having cancer. This method involves detecting, in the subject having cancer, the presence of the K27M mutation in H3 using a diagnostic reagent, where the diagnostic reagent is an K27M H3 antibody, or active binding fragment thereof, of the present invention. As described supra, the antibody has antigenic specificity for the K27M mutation of H3.3 and H3.1. The diagnosis or prognosis of the subject is based on the detection of H3 K27M mutation in the subject.

Detecting the presence of the H3 K27M mutation in the subject using the diagnostic antibody reagent of the present invention can be achieved by obtaining a biological sample from the subject (e.g., tumor, bone-marrow, blood), contacting the biological sample with the diagnostic antibody reagent, and detecting binding of the diagnostic antibody reagent to H3 K27M mutant protein in the sample from the subject. Assays suitable for detecting the H3 K27M mutation in patient samples include, without limitation, western blot, immunohistochemistry, and ELISA, all of which are well known to those of skill in the art.

EXAMPLES

Material and Methods for Examples 1-4

Purification of PRC2 Complex.

Human EED protein containing an N-terminal FLAG-epitope was cloned in pCDH-EF1alpha-IRES-Puro (System Biosciences). Resulting lentivirus were used to establish stable 293T and Hela cell lines that express FLAG-hEED. Nuclear extracts were prepared from washed cell pellets as previously described (Lewis et al., "Daxx is an H3.3-specific Histone Chaperone and Cooperates with ATRX in Replication-Independent Chromatin Assembly at Telomeres," *Proc Natl Acad Sci USA* 107: 14075-14080 (2010), which is hereby incorporated by reference in its entirety). FLAG-M2 immunoprecipitation of clarified nuclear extract was performed, followed by washing (250 mM KCl) and elution with 3XFLAG peptide (400 ng/µL). Eluate from the FLAG M2 beads was loaded onto a Mono Q ion exchange column. Mono Q fractions containing stoichiometric components of PRC2 were pooled.

Purification of Nucleosome Substrates.

HEK293T cells expressing epitope-tagged Histone H3 were hypotonically lysed. Washed nuclei were resuspended in micrococcal nuclease digestion buffer (20 mM HEPES, pH 7.9, 30 mM KCl, 2 mM CaCl2, 0.4 mM PMSF, 3× Protease Inhibitor Cocktail (Roche). Micrococcal nuclease (Worthingtons, 15 U/µL) was added to nuclei, followed by incubation at 30° C. for 5-30 minutes. Reactions were returned to ice, followed by addition of 3 mM EDTA, 3 mM EGTA, 120 mM NaCl, 0.1% Triton. Nuclei were dounced (Wheaton A×10), followed by centrifugation 15K rpm in SS34. FLAG M2 beads were incubated with clarified supernatant at 4° C. Washed beads (150 mM KCl) were eluted with 3× FLAG peptide (50-500 ng/4). DNA from M2 FLAG eluate fractions was resolved by gel electrophoresis for estimation of chromatin lengths. Fractions of similar chromatin (DNA) lengths were pooled and dialyzed (20 mM HEPES, pH 7.9, 10 mM KCl, 10% Glycerol, 0.4 mM PMSF, 0.5 mM DTT).

Methyltransferase Reactions.

Purified PRC2, peptides, and chromatin substrates were added to reaction buffer (50 mM HEPES, pH 7.9, 0.5 mM DTT, 0.4 mM PMSF). Labeled S-adenosyl-methionine (3H-SAM) was added to reactions (225 µM), followed by incubation at 30° C. The reactions were stopped by binding to P81 filter paper (GE Health) for scintillitation counting, or the addition of SDS-PAGE for autoradiography.

Example 1

H3K27Me3 Decreases with Expression of H3K27M

The H3K27M mutation identified in a majority of pediatric DIPGs occurs at a well-studied residue on the H3 N-terminal tail. H3K27 is subject to both acetylation (K27ac) by CBP/P300, and to varying degrees of methylation (K27me1/2/3) by PRC2. The K27M mutation will block post-translational modification on these mutant histone H3 proteins, however, it is unknown how this mutant histone will impact chromatin structure. The heterozygous appearance of H3F3A or HIST3H1B missense mutation at K27, and the exclusive lysine to methionine substitution suggests a gain-of-function for H3 proteins that contain K27M.

Antisera that specifically recognizes the K27M substitution in both H3.1/2 and H3.3 contexts was generated (FIGS. 1A-1D). Using this antibody, acid extracted histones from human DIPG tumors, some of which contained the K27M genetic lesions in H3F3A (H3.3) or HIST3H1B (H3.1) were probed Immunoblots with the K27M-specific antibody on these DIPG histone samples indicated the presence of H3K27M protein (FIG. 1A). Whether DIPG samples that contain the K27M mutation have global changes in histone modification status was also determined. Immunoblots with modification-specific antisera showed that DIPG tumors that contain K27M mutations exhibited decreased H3K27me3, and also a modest increase in levels of H3K27ac (FIG. 1A). The quantities of two transcription-activation related histone modifications (H3K4me3 and H3K36me3) were similar in DIPG samples regardless of tumor genotype.

Whether the presence of H3K27M lead to the striking reduction in H3K27me3 signal in the DIPG samples was then determined. To this end, stable HEK293T cell lines that express FLAG and HA epitope-tagged histone H3.3 or pediatric glioma H3.3 mutants K27M were generated. Additionally, HEK293T cells that express H3.3G34R or G34V, two H3.3-specific missense mutations identified in pediatric GBMs were also generated. Immunoblot on whole cell extracts showed that cells expressing the K27M mutant histone exhibited a decrease in overall K27me3 and K27me2 levels, but showed no change in H3K4me3 or H3K36me3 levels (FIG. 1B). Interestingly, the global loss of H3K27me2/3 was specific to the H3K27M mutation, as no reduction was observed with H3K27R or H3K27Q.

The global reduction in H3K27me2/3 signal suggested that the H3K27M exogenous transgene reduced methylation on endogenous wildtype H3. Chromatin containing H3K27M was purified to examine the post-translational modification status of endogenous histone H3. Mononucleosome populations (>95%) that contain the epitope-tagged H3.3 or K27M were purified by immunoprecipitation with M2-FLAG resin after extensive digestion with micrococcal nuclease. Ponceau stain of immunoprecipitated mononucleosomes resolved by SDS-PAGE show a near 1:1 ratio of epitope-tagged H3.3 to the faster migrating endogenous H3 (FIG. 1C). The post-translational modification status of histone H3.3 in the immunoprecipitated mononucleosomes was probed. Previous work showed that exogenously expressed epitope tagged H3.3 associates exclusively with endogenous H3.3 (Loyola et al., "PTMs on H3 Variants Before Chromatin Assembly Potentiate their Final Epigenetic State," *Mol Cell* 24:309-316 (2006), which is hereby incorporated by reference in its entirety) and it was found that the modification status of the endogenous H3.3 versus the tagged-H3.3 in wildtype nucleosomes was nearly equal for H3K27me3, H3K27ac and H3K36me3 (FIG. 1C). Mononucleosomes that contained an average of one epitope-tagged H3.3K27M histone exhibited a decrease in H3K27me3 on the endogenous H3.3 protein. While these nucleosomes exhibited a decrease in H3K27me3, they showed an increase in the acetylation of H3K27 (H3K27ac) (FIG. 1C). The H3K36me3 levels on the epitope-tagged G34R and G34V histones decreased, however, the levels on the endogenous histone H3.3 remained unchanged (FIG. 1C).

Oligonucleosomes from HEK293T cell lines were purified by limited microcoocal nuclease digestion (>95% of 4-5 nucleosomes in length, with a mode of 2-3 nucleosomes). Ponceau stain of core histones from these arrays suggested the ratio of epitope-tagged H3.3 to endogenous H3 was less than one, indicating that some nucleosomes within the immunoprecipitated arrays contained only endogenous H3 (FIG. 1D). Similar to the mononucleosomes, an increase in the amount of H3K27ac was observed in arrays containing H3.3K27M.

While about 43% of pediatric brain tumors contain the K27M mutation in the H3F3A gene, almost 12% of cases contained the K27M mutation in one gene (HIST1H3B) of the 12 different genes that encode H3.1 (Wu et al., "Somatic Histone H3 Alterations in Pediatric Diffuse Intrinsic Pontine Gliomas and Non-brainstem Glioblastomas," *Nat Genet* 44: 251-253 (2012), which is hereby incorporated by reference in its entirety). Oligonucleosomes purified from HEK293T cells that express epitope-tagged H3.1 also exhibited a decrease in the H3K27me3 signal on neighboring nucleosomes (FIG. 1D).

The invariant nature of the lysine 27 to methionine mutation in nearly 80% of pediatric DIPGs suggests that this amino acid substitution imparts a unique gain-of-function to the mutant histone. A series of amino acid substitutions at H3K27 were constructed to determine if the inhibition of K27me3 on neighboring nucleosomes was unique to K27M. Oligonucleosomes containing K27R (an unmethylatable basic residue) or K27Q (a acetyl-lysine mimic) showed no difference in H3K27me3 on the endogenous H3.3 in immunoprecipitated oligonucleosomes arrays (FIG. 1D). The K27A mutation showed a modest decrease in K27me3 levels on the endogenous H3.3, though reproducibly higher than the K27M mutation.

The immunoprecipitated mono- and oligonucleosomes from HEK293T cells expressing epitope tagged-G34R or G34V exhibited little difference in K27 acetylation or trimethylation. However, these nucleosomes did exhibit a decrease in H3K36m3 on only the epitope-tagged H3.1/3 in either mono- or oligonucleosomes as measured by immunoblot (FIG. 1C, 1D). The observed decrease in H3K36me3 signal on tagged H3G34R/V may result from the destruction of K36me3 antibody epitope. Indeed, the G34R or G34V mutants decreased the immunoblot signal of the H3K36me3 antibody by nearly 10 fold on H3 peptides. Mass spectrometry was used to examine the modification status on H3K36 from immunoprecipitated mononucleosomes. The epitope-tagged H3 exhibited a decrease in K36me2 (~2.5 fold) and K36me3 (~20 fold) on the G34R/V mutants compared to wildtype.

Example 2

H3K27M-Containing Chromatin is a Poor Substrate for PRC2

Figures 2A, 2B, 2C, 2D:
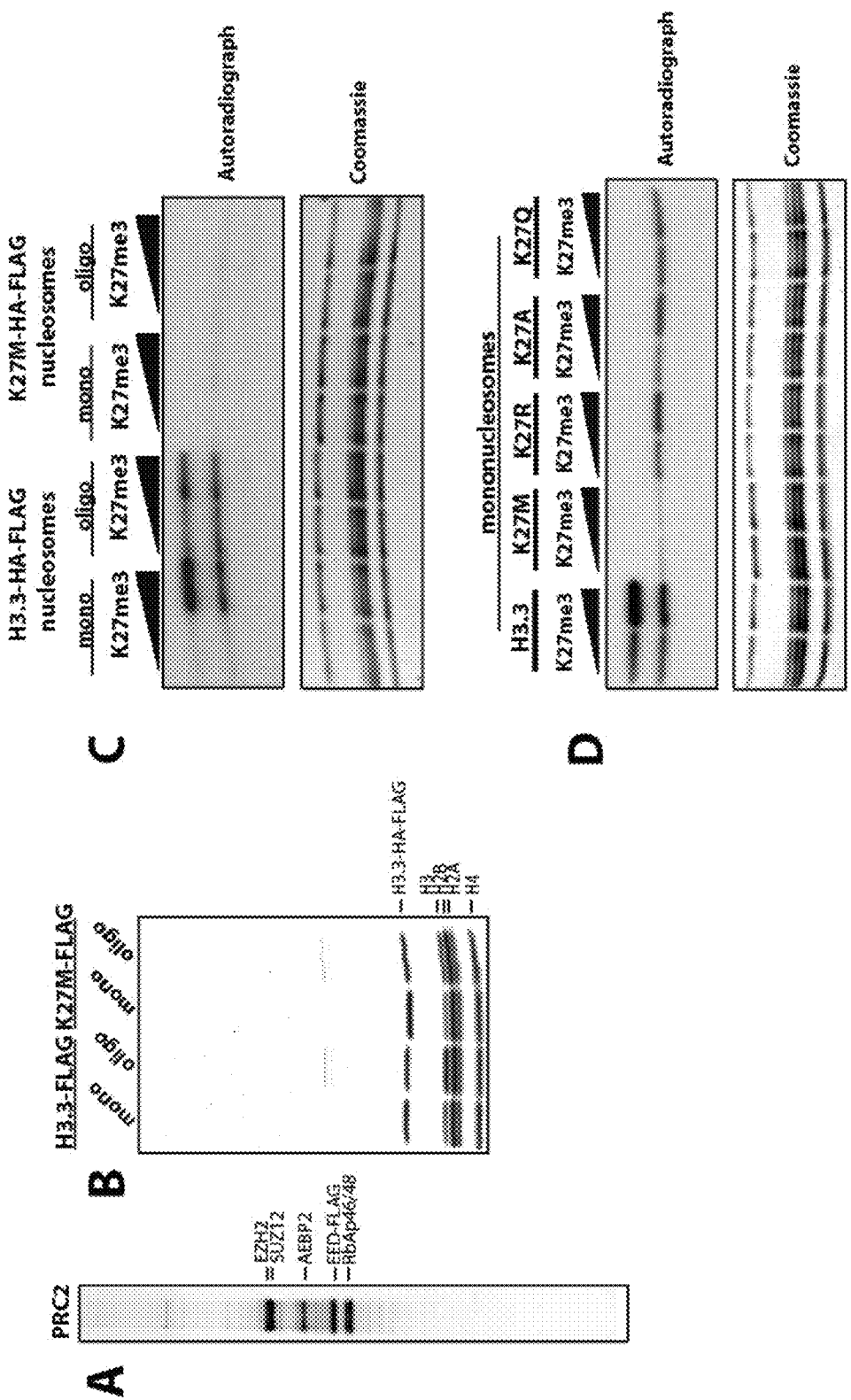
FIGS. 2A-2D demonstrate that H3K27M-containing chromatin is a poor substrate for PRC2.

The decrease in H3K27me2/3 in chromatin containing H3K27M suggests that this template may be a poor substrate for PRC2. To test this hypothesis, recombinant PRC2 was purified from Hela or HEK293T cells that express a FLAG-tagged EED transgene (FIG. 2A). Using purified PRC2 and mono- or oligonucleosomes purified from HEK293T cells (FIG. 2B), histone methyltransferase reactions were performed using radiolabeled SAM. Previous studies found that K27me3 peptides could stimulate PRC2 methyltransferase activity on nucleosome substrates (Margueron et al., "Role of the Polycomb Protein EED in the Propagation of Repressive Histone Marks" *Nature* 461: 762-767 (2009), which is hereby incorporated by reference in its entirety). Allosteric activation of PRC2 activity by the product of its own catalytic activity provides an attractive mechanism for the replication of this important histone modification linked to epigenetic gene silencing. Incubation of 10 or 100 μM of K27me3 peptide strongly stimulated PRC2 activity towards mononucleosome or oligonucleosome templates (FIG. 2C). PRC2 activity on mononucleosome templates that contained on average one epitope tagged H3.3K27M was assessed. Very little PRC2-dependent methylation was detected on the endogenous wild-type H3.3 protein found in K27M mononucleosomes (FIG. 2C). Similarly, oligonucleosomes containing K27M also showed decrease PRC2-dependent methylation as compared to wildtype H3.3 oligonucleosomes.

The K27M mutation uniquely decreased the levels of H3K27me3 on nucleosome arrays immunoprecipitated from 293T cells (FIG. 1C, D). Methyltransferase assays on different mononuclesome templates were performed to determine if the reduced PRC2 activity on H3.3 present in FIG. 2C was unique to K27M mononucleosomes. Mononucleosomes containing the K27M mutation exhibited the least amount of methylation as compared to templates with K27Q, K27R or K27A (FIG. 2D). However, mononucleosomes with K27R, K27Q or K27A showed a modest reduction in methylation on the endogenous H3.3 protein relative to wildtype H3.3 mononucleosomes.

Example 3

H3K27M Peptide Inhibits PRC2 Activity in Trans

Figure 3A:
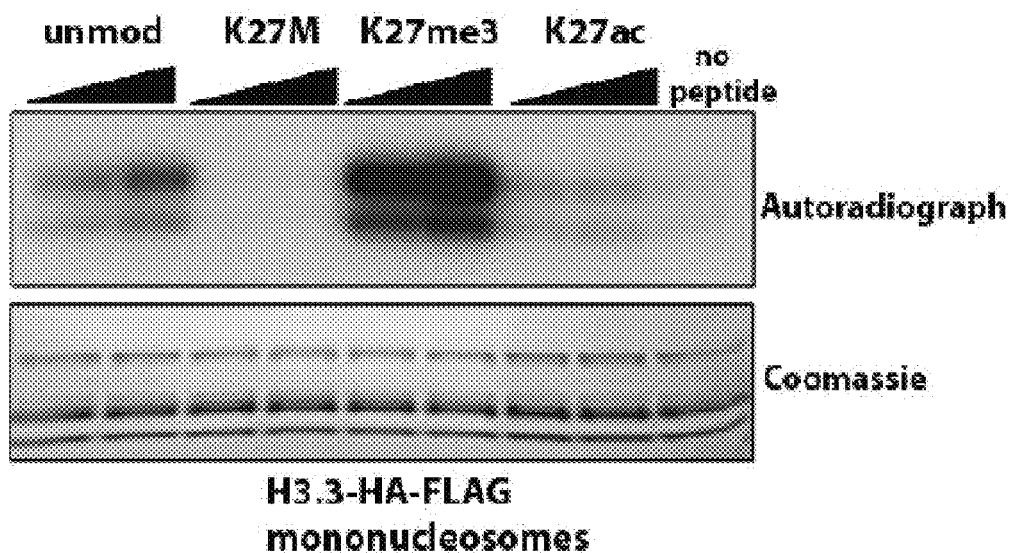
FIGS. 3A-3F show inhibition of PRC2 activity by H3K27M peptide in trans.
Figure 3B:
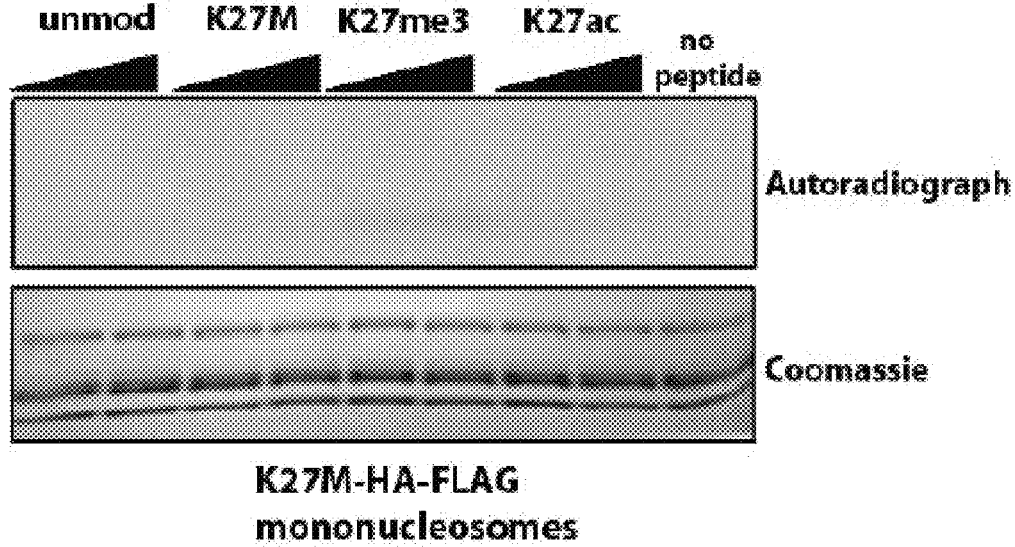
Figure 3C:
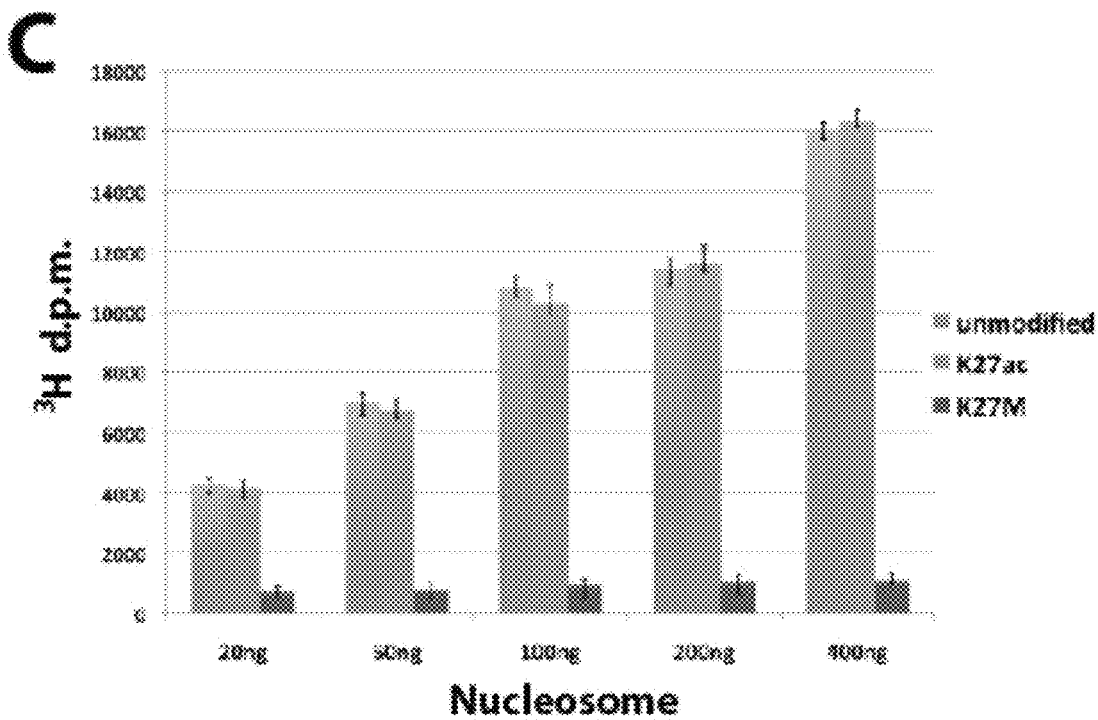

The reduced methylation on nucleosome templates suggests that the K27M peptide may interfere with PRC2 activity. Previously, peptides from histone H1K26me3 were shown to inhibit PRC2 methyltransferase activity on nucleosome templates in trans (Xu et al. "Binding of Different Histone Marks Differentially Regulates the Activity and Specificity of Polycomb Repressive Complex 2 (PRC2)," Proc Natl Acad Sci USA 107: 19266-19271 (2010), which is hereby incorporated by reference in its entirety). Whether H3.3K27M peptides could interfere with PRC2 activity when added in trans was determined. The K27me3 peptide strongly stimulated PRC2 activity, whereas unmodified or K27ac peptide exhibited little stimulation relative to the no peptide control (FIG. 3A). Incubation of K27M peptide decreased PRC2 activity on nucleosomes to below the no peptide signal (FIG. 3A). Incubation of this same set of peptides using a H3.3K27M-containing nucleosome template showed little or undetectable methylation on the endogenous H3.3 (FIG. 3B).

Figure 3D:
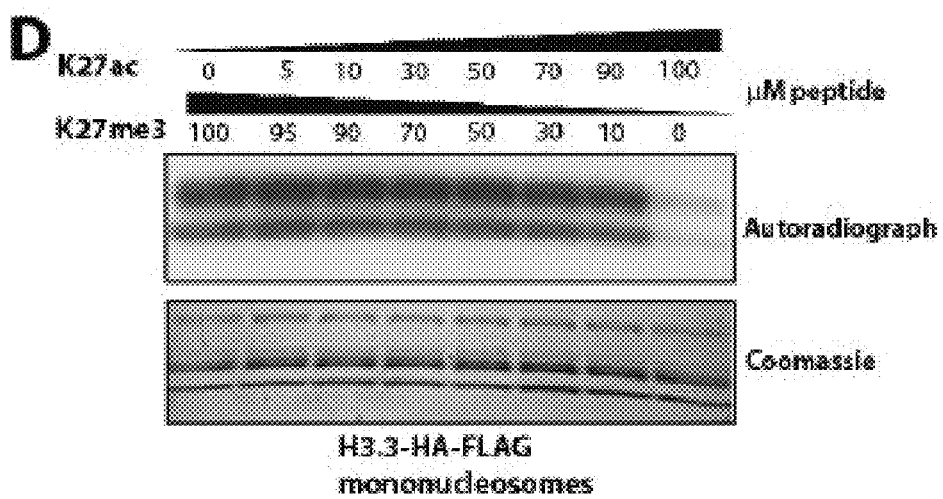
Figures 3E, 3F:
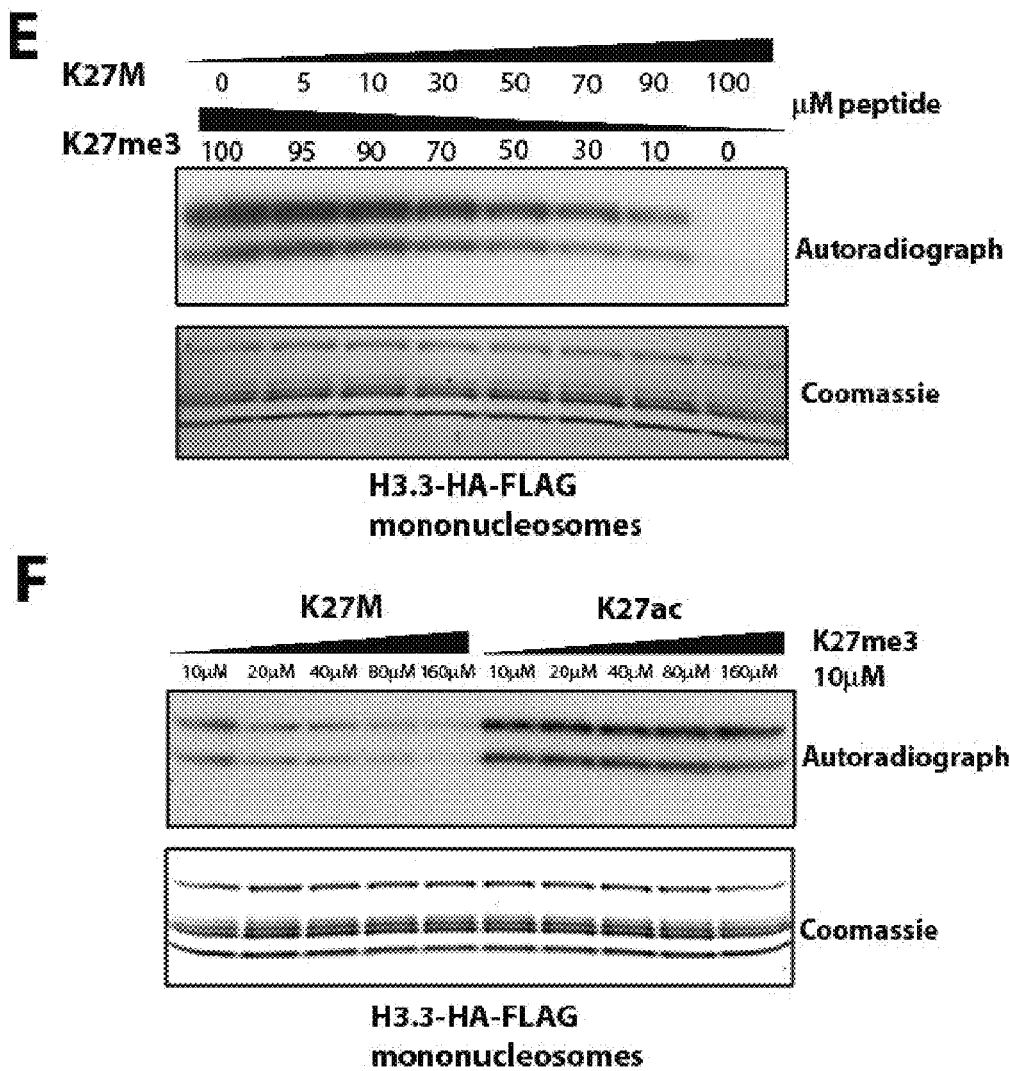

An increasing concentration of K27M or K27ac peptide was titrated, while the concentration of K27me3 peptide was simultaneously decreased. A modest decrease in PRC2 activity at a K27M:K27me3 ratio of 1:2.3 was observed that steadily grew with an increased ratio of K27M to K27me3 peptide. In contrast, no decrease in PRC2 activity was observed at a 9:1 ratio of K27ac: K27me3 peptide (FIG. 3D, 3E). The inhibitory effect of the K27M peptide became more pronounced with titration of K27M into PRC2 reactions containing a constant low concentration of K27me3 peptide (FIG. 3F). Again, no decrease in PRC2 activity was observed with a titration of the K27ac peptide. These data confirm that the K27M peptide is an inhibitor of PRC2 activity.

Example 4

Figure 4A:
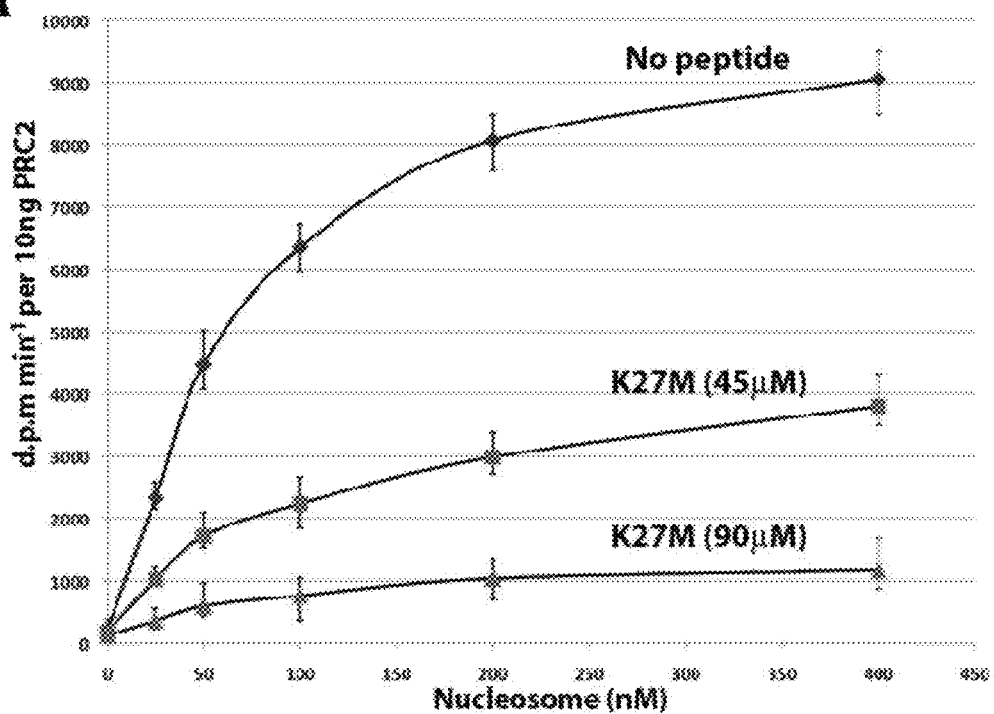
FIGS. 4A-4B demonstrate that H3K27M peptides exhibit mixed non-competitive inhibition of PRC2 methyltransferase activity. In the graph of FIG. 4A the initial reaction rates from assays with PRC2 were determined at various nucleosome concentrations. The assays were performed without, and with the H3K27M peptide at two concentrations.
Figure 4B:
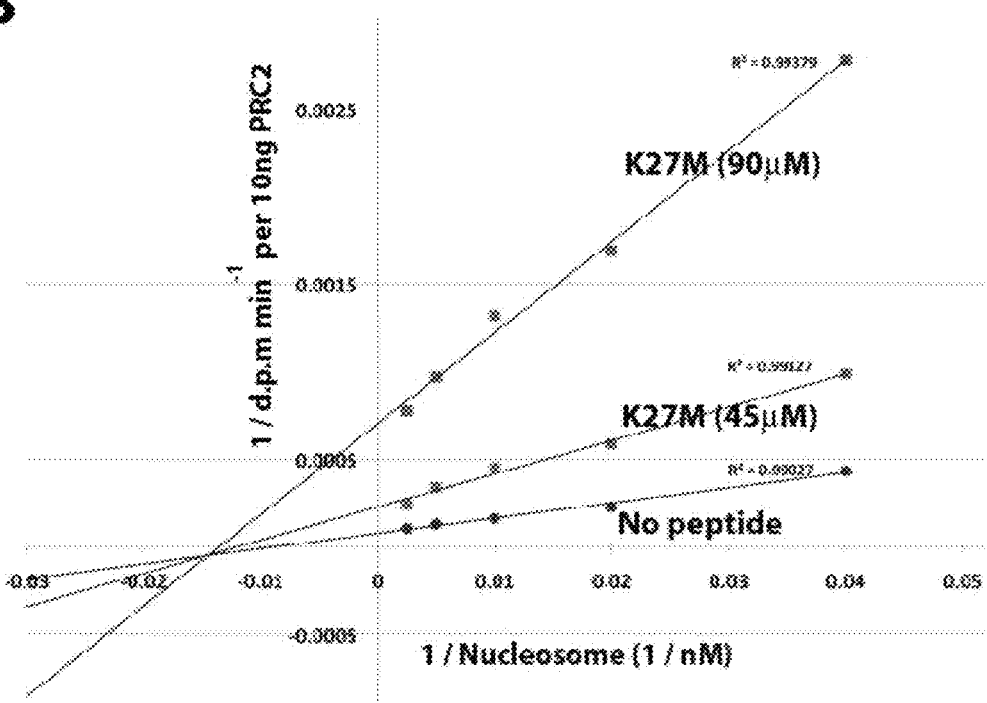

H3K27M Peptides Exhibit Mixed Non-Competitive Inhibition of PRC2 Methyltransferase Activity Kinetic studies were performed to better understand the inhibitory effect of the K27M peptide on PRC2 activity. Time course of PRC2 methyltransferase assays with varying mononucleosome substrate concentrations were performed without or with K27M peptide at two different concentrations (FIG. 4A). Plotting the initial velocity versus nucleosome substrate concentration showed a reduction in the apparent Vmax by addition of the K27M peptide. PRC2 reactions that contained H3K27ac peptide of identical peptide concentrations did not decrease the apparent Vmax of the reaction. A double reciprocal Lineweaver-Burke plot of the initial velocity versus substrate plot showed that H3K27M primarily affects the Vmax of the reaction, while having little effect on the Km of the substrate. These data are consistent with a non-competitive inhibition model for the H3K27M peptide. The Ki for the H3K27M was calculated to be 21 µM.

Example 5

Inhibition of H3K27 Methylation is Specific to the H3K27M Containing Peptide

Figures 5A, 5B, 5C, 5D:
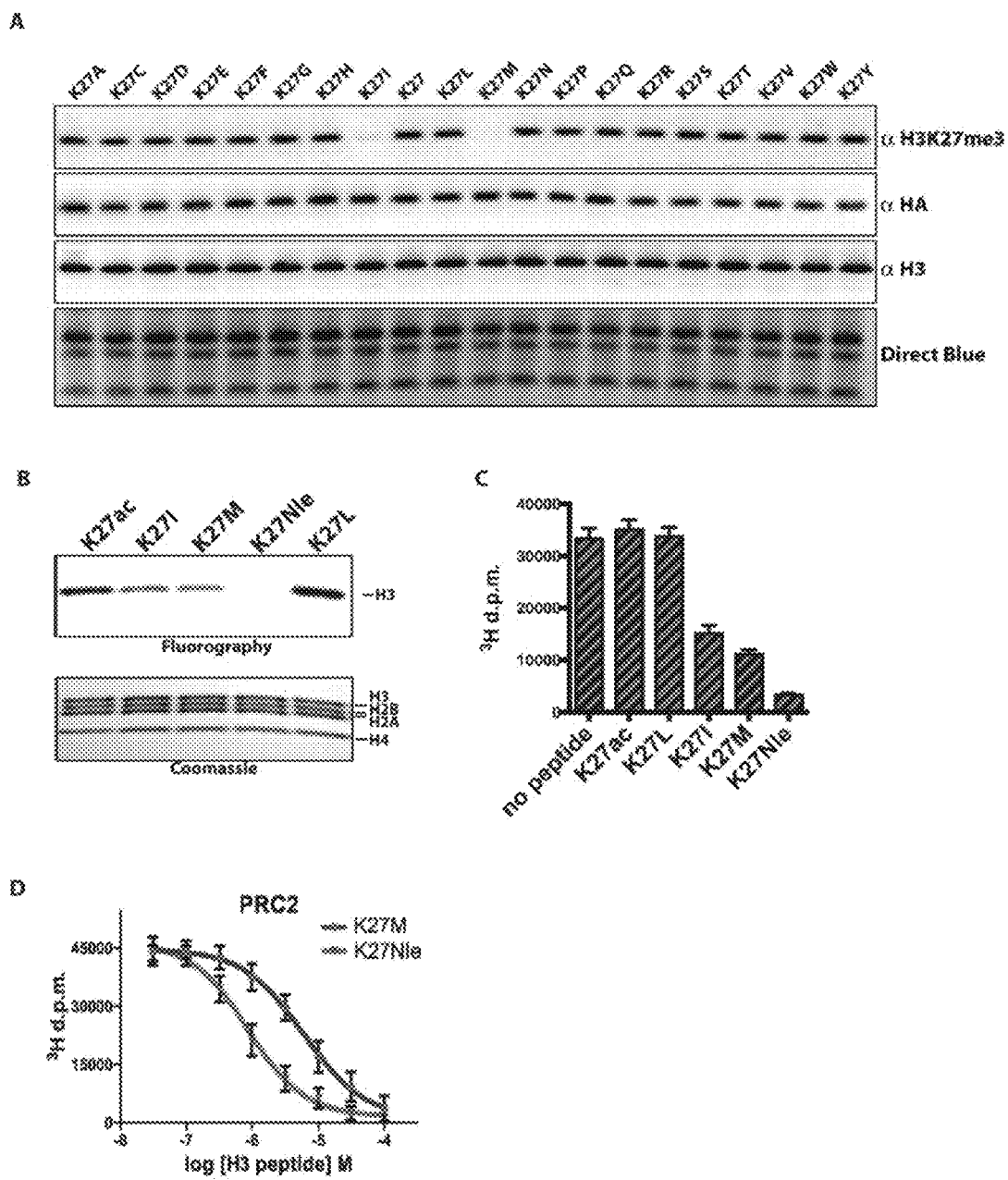
FIGS. 5A-5D show that inhibition of H3K27 methylation is specific to the H3K27M containing peptide.

The heterozygous and invariant nature of the lysine-to-methionine mutation at residue 27 in nearly 80% of pediatric DIPGs strongly suggests that this specific amino acid substitution imparts a unique gain-of-function to the mutant histone. To further test the specificity of this substitution, a survey of all amino acid substitutions at H3K27 was performed. Nearly all substitutions had little effect, if any, on the amounts of K27me3, with the exception of methionine, and to a lesser extent isoleucine (FIG. 5A). Titration of K27M peptide to in vitro methylation reactions revealed a median inhibitory concentration ($IC_{50}$) of 5.9 µM [95% confidence interval (CI) of 1.10 to 6.42]. Peptides containing $Lys^{27}$ replaced by Ile inhibited PRC2 to a lesser extent than K27M ($IC_{50}$ for K27I=8.9 µM (95% CI: 4.12 to 11.2), whereas $Lys^{27}$ replaced by Leu had no inhibitory effect on the amounts of H3K27me3 in vivo or PRC2 in vitro (FIGS. 5B and 5C). To evaluate whether the thioether moiety of methionine was required for inhibition of PRC2, a norleucine derivative (K27Nle) was prepared. The K27Nle variant proved to be an even better inhibitor of PRC2. ($IC_{50}$ for K27Nle=0.85 µM) (95% CI: 0.57 to 1.27) (FIG. 5D). Thus, a long, hydrophobic residue suffices for EZH2 binding, and methionine—and to a slightly lesser extent isoleucine—represents the ideal biochemically accessible choices.

To carry out the experiments described above, human 293T, 293 or murine PDGF-transduced glioblastoma cells were transduced with recombinant, concentrated Lentivirus made with the pCDH-EF1-MCS-Puro or Neo expression vector (5 µg/mL polybrene, 2×10^7 IFU). Transduced cells were grown under selection (1 µg/mL Puromycin or 0.8 µg/mL G418) at 24 hours post transduction for 72 hours. Cells were collected at 7-10 days post transduction for immunoblot analysis. The amino acid sequence of epitope tagged-H3.3 used in transgenic experiments is shown below as SEQ ID NO: 57. The C-terminal FLAG and HA epitope sequences are shown in bold.

(SEQ ID NO: 57)
MARTKQTARKSTGGKAPRKQLATKAARKSAPSTGGVKKPHRYRPGTVALR

EIRRYQKSTELLIRKLPFQRLVREIAQDFKTDLRFQSAAIGALQEASEAY

LVGLFEDTNLCAIHAKRVTIMPKDIQLARRIRGERAAAAGGDYKDDDDKS

AAGGYPYDVPDA

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated peptide comprising an amino acid sequence of XAARMSXPXXG (SEQ ID NO:4), wherein X is any amino acid residue, wherein said peptide is between 10-50 amino acids in length, and wherein the peptide is acetylated at the N-terminus and amidated at the carboxy terminus.

2. The isolated peptide of claim 1, wherein X at position 1 is a lysine or arginine residue, X at position 7 is an alanine or serine residue, and X at position 9 and position 10 is a serine, alanine, or threonine residue.

3. The isolated peptide of claim 1, wherein said peptide comprises the amino acid sequence of TXAARMSXPXXG-GVK (SEQ ID NO: 41).

4. The isolated peptide of claim 1, wherein said peptide comprises the amino acid sequence of KQLATXAARMSX-PXXGGVKK (SEQ ID NO: 44).

5. A fusion peptide comprising:
    an isolated peptide that is between 10-50 amino acids in length and comprises an amino acid sequence of XAARMSXPXXG (SEQ ID NO:4), wherein X is any amino acid residue;
    and one or more targeting moieties coupled to the isolated peptide.

6. The fusion peptide of claim 5, wherein the targeting moiety is a cell specific targeting moiety.

7. The fusion peptide of claim 5, wherein the targeting moiety is a cell uptake moiety.

8. The fusion peptide of claim 7, wherein the cell uptake moiety comprises a trans-activator of transcription (TAT) protein or peptide thereof.

9. The fusion peptide of claim 5, wherein the targeting moiety is a nuclear localization moiety.

10. A pharmaceutical composition comprising:
    the isolated peptide of claim 1 and
    a pharmaceutically acceptable carrier.

11. The pharmaceutical composition of claim 10 further comprising:
    a delivery vehicle.

12. A method of treating a subject having cancer comprising:
    selecting a subject having cancer, wherein said cancer is selected from the group consisting of leukemia, lymphoma, breast cancer, melanoma, bladder cancer, gastric cancer, endometrial cancer, prostate cancer, Ewing sarcoma, and non-small cell lung cancer; and administering the isolated peptide of claim 1 to the subject under conditions effective to treat the cancer.

13. The method of claim 12, wherein said cancer is mediated by increased PRC2 activity.

14. The method of claim 12, wherein X at position 1 of SEQ ID NO: 4 is a lysine or arginine residue, X at position 7 is an alanine or serine residue, and X at position 9 and position 10 is a serine, alanine, or threonine residue.

15. The method of claim 12, wherein said peptide comprises the amino acid sequence of TXAARMSXPXXGGVK (SEQ ID NO: 41).

16. The method of claim 12, wherein said peptide comprises the amino acid sequence of KQLATXAARMSX-PXXGGVKK (SEQ ID NO: 44).

17. A method of treating a subject having cancer comprising:
    selecting a subject having cancer, wherein said cancer is selected from the group consisting of leukemia, lymphoma, breast cancer, melanoma, bladder cancer, gastric cancer, endometrial cancer, prostate cancer, Ewing sarcoma, and non-small cell lung cancer; and administering the fusion peptide of claim 5 to the subject under conditions effective to treat the cancer.

* * * * *